US009758552B2

(12) United States Patent
Gillet et al.

(10) Patent No.: US 9,758,552 B2
(45) Date of Patent: Sep. 12, 2017

(54) **HB-EGF INHIBITOR DERIVED FROM THE R DOMAIN OF DIPHTHERIA TOXIN FOR THE TREATMENT O of diphtheria toxin, which can be used for the treatment and diagnosis of diseases involving the activation of the HB-EGF/EGFR pathway.

14 Claims, 7 Drawing Sheets

(51) Int. Cl.

| | |
|---|---|
| *C07K 14/34* | (2006.01) |
| *A61K 38/16* | (2006.01) |
| *C12N 9/10* | (2006.01) |
| *G01N 33/74* | (2006.01) |
| *A61K 38/00* | (2006.01) |
| *A61K 48/00* | (2006.01) |

(52) U.S. Cl.
CPC .............. *A61K 38/00* (2013.01); *A61K 48/00* (2013.01); *C12Y 204/02036* (2013.01)

(56) References Cited

U.S. PATENT DOCUMENTS

| | | | |
|---|---|---|---|
| 6,455,673 | B1 | 9/2002 | Collier |
| 2003/0050447 | A1 | 3/2003 | Collier |
| 2009/0105135 | A1 | 4/2009 | Mekada et al. |

FOREIGN PATENT DOCUMENTS

| | | | |
|---|---|---|---|
| WO | 95 33481 | 12/1995 | |
| WO | 00 48638 | 8/2000 | |
| WO | WO 0112661 A2 * | 2/2001 | ............. C07K 14/34 |

OTHER PUBLICATIONS

Lobeck, K., et al., "Towards a Recombinant Vaccine against Diphtheria Toxin", Infection and Immunity, vol. 66, No. 2, pp. 418-423, (Feb. 1998) XP 002687264.
Shen, W.H., et al., "Participation of Lysine 516 and Phenylalanine 530 of Diphtheria Toxin in Receptor Recognition", The Journal of Bilogical Chemistry, vol. 269, No. 46, pp. 29077-29084, (Nov. 18, 1994) XP 002153861.
Buzzi, S., et al., "CRM197 (nontoxic diphtheria toxin): effects on advanced cancer patients", Cancer Immunol Immunother, vol. 53, vol. 11, pp. 1041-1048, (Nov. 1, 2004) XP 002475696.
Louie, G.V., et al., "Crystal Structure of the Complex of Diphtheria Toxin with an Extracellular Fragment of Its Receptor", Molecular Cell, vol. 1, No. 1, pp. 67-78, (Dec. 1997) XP 002687267.
Miyazono, K., "Ectodomain shedding of HB-EGF: A potential target for cancer therapy", J. Biochem., vol. 151, No. 1, pp. 1-3, (Jan. 2012) XP 002687266.
Villiers, B., et al., "Engineering of an HB-EGF Inhibitor from the Diphtheria Toxin Receptor-Binding Domain for the Treatment of HB-EGF-Related Diseases", Toxicon, vol. 60, No. 2, pp. 106-107, (Aug. 2012) XP 002687265.
International Search Report Issued Jun. 6, 2013 in PCT/IB13/052173 Filed Mar. 19, 2013.

* cited by examiner

HB-EGF INHIBITOR DERIVED FROM THE R DOMAIN OF DIPHTHERIA TOXIN FOR THE TREATMENT OF DISEASES ASSOCIATED WITH THE ACTIVATION OF THE HB-EGF/EGFR PATHWAY

The present invention relates to a ligand recombinant protein inhibiting HB-EGF (Heparin-Binding Epidermal Growth Factor-like growth factor), derived from the R domain of diphtheria toxin, of use for the treatment and diagnosis of diseases involving the activation of the HB-EGF/EGFR pathway.

HB-EGF is a growth factor expressed at the surface of the cells of the organism in the form of a precursor membrane protein, pro-HB-EGF, which is the natural diphtheria toxin receptor.

Diphtheria toxin (DT) is an exotoxin of 535 amino acids (SEQ ID NO: 1) composed of a fragment A (N-terminal) and of a fragment B (C-terminal). Fragment A comprises the catalytic domain (C or DTA/DT-A; residues 1 to 193) and fragment B comprises the translocation domain (T; N-terminal; residues 202 to 378), and the cell receptor-binding domain (R or DTR; C-terminal; residues 379-386 to 535). DT binds to the surface of cells via the binding of its R domain to pro-HB-EGF; after activation of DT by proteolytic cleavage between fragments A and B, the T domain allows translocation of fragment A into the cytoplasm. Once in the cytoplasm, the catalytic domain carried by fragment A blocks protein synthesis by inactivating the EF2 elongation factor, thus causing cell death. The study of natural or synthetic mutants of DT has shown that the binding of DT to the pro-HB-EGF receptor is abolished by the substitution of residue S508 (S508F) or of residues of the loop of the region K516-F530 of DTR (K516A, K516E, F530A, F530S and S525F), but not by the deletion of the 4 C-terminal residues (residues E532-S535; Shen et al., J. Biol. Chem., 1994, 269, 29077-29084). In addition, the natural mutant of DT comprising the G52E mutation, called CRM197, has a greatly reduced catalytic activity (Giannini et al., N.A.R., 1984, 12, 4063-4069).

During inflammatory processes involving HB-EGF, the pro-HB-EGF membrane protein is cleaved by a protease and HB-EGF is released from the cell surface, in the form of a secreted protein. It then binds in an autocrine or paracrine manner to the ErbB1 (HER1 or EGFR) and ErbB4 (HER4) subunits of the EGF receptor family (EGFR family or EGFR), expressed in virtually all the tissues of the organism. There are at least ten EGFR ligands in addition to HB-EGF, namely EGF, TGF-alpha, amphiregulin, betacellulin, epigen, epiregulin and neuregulins −1, −2, −3 and −4. It is the local context which determines the stimulation of EGFR by one or the other of these ligands.

The activation of the HB-EGF/EGFR pathway which is associated with increased expression of pro-HB-EGF and/or the release of HB-EGF leads to deleterious cell proliferation responsible for numerous pathological conditions:

rapidly progressive glomerulonephritis (RPGN) during which the proliferation of the glomerular renal cells (podocytes) results in kidney destruction (Feng et al., J. Clin. Invest., 2000, 105, 341-350; Bollee et al., Nat. Med., 2011, 17, 1242-1250), cancers, including ovarian cancer, endometrial cancer, breast cancer, uterine cancer (uterine adenocarcinoma), bladder cancer, stomach cancer, skin cancer (malignant melanoma), brain cancer (glioblastoma) and lung cancer (Yotsumoto et al., Biochem Biophys Res Commun, 2008, 365, 555-561; Miyamoto et al., Adv. Exp. Med. Biol., 2008, 622, 281-295; Miyamoto et al., Anticancer Res., 2009, 29, 823-830; Fu et al., Proc. Natl. Acad. Sci. U S A, 1999, 96, 5716-5721; Tsujioka et al., Anticancer. Res., 2010, 30, 3107-3112), vasospasm associated with cerebral contusions (Chansel et al., FASEB J., 2006, 20, 1936-1938), cardiac hypertrophy (Asakura et al., Nat. Med., 2002, 8, 35-40; Hamaoka et al., J. Biochem., 2010, 148, 55-69), smooth muscle cell hyperplasia (Miyagawa et al., J. Clin. Invest., 1995, 95, 404-411; Hamaoka et al., J. Biochem., 2010, 148, 55-69), pulmonary hypertension (Powell et al., Am. J. Pathol., 1993, 143, 784-793; Hamaoka et al., J. Biochem., 2010, 148, 55-69), diabetic retinopathies, and arterial restinosis.

Because of its involvement in an increasing number of diseases, HB-EGF represents a therapeutic target. There are currently two types of molecules available for blocking the action of HB-EGF on the EGFR, EGFR inhibitors and HB-EGF inhibitors. These molecules which are potentially usable for treating pathological conditions involving EGFR activation by HB-EGF (HB-EGF/EGFR pathway) have, however, a certain number of major drawbacks.

EGFR Inhibitors

Two types of EGFR inhibitors could theoretically be used to block EGFR stimulation by HB-EGF: reversible tyrosine kinase inhibitors which act on the EGFR, such as erlotinib, and antibodies directed against the EGFR, such as cetuximab (Ciardiello and Tortora, N. Engl. J. Med., 358, 1160-1174; WO 2008/053270).

However, these molecules which act on the tyrosine kinase of the EGFR (small molecules) or on the EGFR itself (monoclonal antibodies) are not specific for the HB-EGF/EGFR pathway, given that they block the activation of the EGFR irrespective of the origin of its stimulation, independently of the ligand activating it and irrespective of this ligand. Because of their lack of specificity, EGFR inhibitors produce significant side effects. By way of example, mention may be made of the following side effects reported, respectively, for erlotinib and cetuximab: neutropenia, thrombocytopenia, anemia, edema, nausea, vomiting, headaches, pruritus and musculoskeletal pain; fever, shivering, urticaria, pruritus, skin rash, hypotension, bronchospasm, dyspnea, edema, confusion, anaphylactic shock and cardiac arrest.

Furthermore, antibodies are too big (150 kDa) to reach their target in the case of RPGN given that the EGFR stimulated by HB-EGF is expressed by the podocytes in the kidney glomeruli and that the glomerular filtration threshold is approximately 68 kDa. Likewise, the penetration of antibodies into solid tumors is limited owing to their size.

HB-EGF Inhibitors

In mice, knockout of the pro-HB-EGF gene prevents the triggering of induced RPGN (Bollee et al., Nat. Med., 2011, 17, 1242-1250), thus justifying the advantage of developing a ligand inhibiting HB-EGF and pro-HB-EGF for the treatment of pathological conditions involving the activation of the HB-EGF/EGFR pathway.

There are currently two types of HB-EGF inhibitors potentially usable for blocking EGFR stimulation by HB-EGF: antibodies directed against HB-EGF (WO 2009/040134; WO 2011/21381; WO 2009/72628; EP 2221374; EP 2281001; EP 2093237; EP2078731; EP 2039704; WO 2008/053270) and CRM197 (U.S. Pat. No. 7,700,546; US 2006/0270600).

The antibodies directed against HB-EGF are more specific than the EGFR inhibitors given that they block only the activation of the HB-EGF/EGFR pathway, but they have the same drawbacks as the anti-EGFR antibodies, linked to their excessive size.

CRM197 is a natural ligand of HB-EGF capable of blocking its binding to the EGFR. It is currently used in clinical trials to block HB-EGF in order to combat ovarian cancer (Koshikawa et al., Cancer Sci., 2011, 102, 111-116; Tsujioka et al., Anticancer Res., 2011, 31, 2461-2465).

However, CRM197 has drawbacks in terms of residual toxicity, size, affinity, immunogenicity and antigenicity.

The residual toxicity of CRM197 is $10^6$ times lower than that of the wild-type diphtheria toxin (Kageyama et al., J. Biochem., 2007, 142, 95-104). This is, however, not insignificant since the wild-type toxin is extremely powerful with a lethal dose 50 (LD50) of 5 pM in primate cell culture. CRM197 is therefore toxic at micromolar (µM) doses. This can present a risk if it is administered to humans at high dose (Kageyama et al., J. Biochem., 2007, 142, 95-104).

CRM197 has a molecular weight of 58 kDa, passing the glomerular filtration threshold with difficulty. It cannot therefore be used to treat RPGN or other pathological conditions such as solid tumors, where tissue penetration is an important factor for therapeutic efficacy.

CRM197 has a medium affinity for HB-EGF (Kd=27 nM; Brooke et al., Biochem. Biophys. Res. Commun., 1998, 248, 297-302). This affinity is lower than that of a good therapeutic antibody.

CRM197 is very immunogenic. It differs from diphtheria toxin only by one residue (G52E). It therefore carries all of the CD4 T epitopes of diphtheria toxin, or almost, if the mutation affects a T epitope. As it happens, western populations are vaccinated against diphtheria toxin. Treating patients with CRM197 amounts to giving a vaccination booster. As early as the first injection, CRM197 can cause the reactivation of memory CD4 T cells and can restimulate the production of circulating antibodies. A few days after the first administration of CRM197, these antibodies should neutralize the protein and make the treatment ineffective.

CRM197 is very antigenic since it has virtually all the B epitopes of diphtheria toxin. Since the western population is vaccinated against diphtheria toxin, a significant fraction of individuals have circulating antibodies capable of neutralizing CRM197 as early as the first administration. This imposes the use of massives doses of CRM197 in order to obtain a therapeutic effect, while considerably increasing the risks of side effects (toxicity, anaphylactic shock, etc.)

Consequently, there is a real need to have new HB-EGF inhibitors which have a smaller size, a better affinity for HB-EGF, and a reduced antigenicity, immunogenicity and toxicity, compared with CRM197.

Up until now, it has not been possible to produce the isolated DTR domain, directly, in recombinant form, with a high yield, and without using detergents or chaotropic or denaturing agents to extract the recombinant protein from the transformed cells.

Indeed, in order to stabilize the structure of the isolated DTR domain, and to improve the extraction and purification of this domain from the transformed bacteria, it is essential to fuse the DTR domain to a protein (glutathione-S-transferase, GST) or to a protein domain (ZZ domain derived from S. aureus protein A (Lobeck et al., Infect. Immun., 1998, 66, 418-423; Shen et al., J. Biol. Chem., 1994, 269, 29077-29084). In addition, mutants of the loop of region 516-530 of DTR have been produced using the GST-DTR fusion; these DTR mutants are incapable of binding to the pro-HB-EGF receptor (Shen et al., 1994).

In the abovementioned two cases, the recombinant protein produced in E. coli is not an isolated DTR domain, but a GST-DTR or ZZ-DTR fusion protein. In the case of the GST-DTR fusion protein, the production yields are mediocre and it is essential to use a detergent (1% Triton X-100) to extract the fusion protein from the transformed bacteria. Furthermore, in order to produce a therapeutic protein, the fusion partner must be removed, thereby making the production process much more complex and even further reducing yields.

The inventors have constructed mutants of the isolated DTR domain, devoid of fusion-partner sequences. These mutants of the isolated DTR domain are expressed directly and in a large amount in the form of a soluble recombinant DTR protein of small size (approximately 17500 Da) with affinity for pro-HB-EGF and HB-EGF. These DTR mutants have been modified to produce improved recombinant DTR proteins which, surprisingly, have both a reduced antigenicity and immunogenicity and a considerably increased affinity, compared with CRM197.

Consequently, a subject of the present invention is a recombinant protein comprising an amino acid sequence having at least 70% similarity with residues 380 to 535 of the amino acid sequence SEQ ID NO: 1 which correspond to the R domain of diphtheria toxin, said sequence comprising the substitution of at least one, preferably at least two, of the residues Y380, P382, Q387, P388 and/or L390 of said R domain with another amino acid selected from the group consisting of: S, T, N, C, Y, Q, R, K, H, D and E, and said sequence being devoid, at the N- or C-terminal end of said R domain, of the sequence of the T domain or of the C domain and of the T domain of diphtheria toxin and of the sequence of a protein or of a protein domain capable of improving the stability or the purification of said R domain, and said recombinant protein being a ligand inhibiting HB-EGF.

The invention provides a therapeutic recombinant protein that is a ligand of HB-EGF and of pro-HB-EGF, which has the following advantages:

it has a greatly increased solubility compared with the wild-type form $DTR_{WT}$. The substitution of at least one, preferably at least two, of the residues Y380, P382, Q387, P388 and/or L390 with a different hydrophilic, polar or charged amino acid residue as defined above makes it possible to considerably increase the solubility of the DTR protein in aqueous solution. Thus, the recombinant protein according to the invention can be extracted from the host cells and purified without using detergents or chaotropic or denaturing agents. By comparison, the wild-type DTR protein ($DTR_{WT}$) produced in the same expression system is insoluble and not solubilized using detergents compatible with therapeutic use. The $DTR_{WT}$ protein is solubilized in the presence of 0.5% of sarkosyl or sodium dodecyl sulfate, which are detergents that are incompatible with therapeutic use at these concentrations;

it is much easier to produce in recombinant form than $DTR_{WT}$. It is produced directly, without using a fusion partner for improving the stability or the purification of the R domain. It is produced in E. coli according to standard fermentation procedures, in a folded soluble form, and in a large amount after final purification (several tens of mg/l of culture under nonoptimized laboratory conditions);

it has an affinity for HB-EGF and pro-HB-EGF which is at least 10 times greater than that of CRM197. Surprisingly, although the wild-type DTR protein ($DTR_{WT}$) has an affinity for HB-EGF and pro-HB-EGF which is 2-fold lower than that of CRM197, the mutant DTR proteins according to the invention have an affinity for HB-EGF and pro-HB-EGF that is considerably higher than that of CRM197; the proteins called DTR1, DTR3 and DTR8 have, respectively, an affinity which is 60, 300 and 1400 times higher than that of CRM197. This means that DTR8 could be used at doses much lower than CRM197 for the same therapeutic effect. As a result, the risks of side effects, linked in general to the existence of low-affinity binding with other proteins or ligands of the organism, are therefore considerably reduced by comparison with CRM197. These interactions are eliminated by using low doses, of the order of one pM, which should be the case for DTR8;

it has a reduced immunogenicity compared with CRM197 and with $DTR_{WT}$. Ten of the 26 T epitopes identified in $DTR_{WT}$ have been deleted from the DTR8 protein by site-directed mutagenesis, including 7 among 9 immunodominant epitopes;

it has a greatly reduced antigenicity compared with CRM197 and with $DTR_{WT}$. The sera of individuals vaccinated against diphtheria toxin preferentially recognize the catalytic domain of said toxin. This domain is present in the CRM197 molecule and absent from the mutated DTR protein according to the invention. Moreover, the mutated DTR protein according to the invention is not as well recognized as $DTR_{WT}$ by the antibodies of vaccinated subjects which recognize $DTR_{WT}$;

it blocks a pathway of EGFR (ErbB1 and ErbB4) activation by HB-EFG much more specifically than the commercial EGFR inhibitors (therapeutic antibodies and small molecules), as a result presenting potentially much less risk of side effects;

it is small in size; the proteins of SEQ ID NOs: 2 to 9 have a sequence of 158 amino acids and an MW of approximately 17 500 Da, i.e. a size 3.4 times smaller than that of CRM197 and 8.8 times smaller than that of the anti-HB-EGF antibodies currently used in clinical protocols for blocking the HB-EGF pathway. As a result of its small size, the recombinant protein according to the invention is more effective in the treatment of pathological conditions associated with the activation of the HB-EGF pathway, in particular RPGN or ovarian cancer, since it diffuses more readily in the tissues, in particular tumors, and is capable of penetrating into kidney glomeruli.

In addition, because of its high affinity for HB-EGF and pro-HB-EGF, the protein according to the invention can also be used for the diagnosis of diseases involving the activation of the HB-EGF/EGFR pathway.

Definitions

In the present application, the term "DTR" or "DTR domain" is intended to mean the R domain of diphtheria toxin which corresponds to residues 380-385 to 531-535 of the amino acid sequence of wild-type diphtheria toxin (SEQ ID NO: 1).

The expression "DTR protein" denotes a recombinant protein comprising an isolated DTR domain, i.e. which is devoid, at its N- or C-terminal end, of the sequence of the T domain or of the C domain and of the T domain of diphtheria toxin and of the sequence of a protein or of a protein domain capable of improving the stability or the purification of said R domain. In addition, the purification of the R domain includes the extraction and the purification of said domain, given that it is produced in the form of a recombinant protein.

The recombinant protein according to the invention which comprises at least one, preferably at least two, substitution(s) as defined above is denoted mutant DTR protein, mutated DTR protein or $DTR_n$ protein where n is an integer, as opposed to the wild-type DTR recombinant protein ($DTR_{WT}$) which does not comprise this substitution.

The amino acids are denoted using the one-letter code.

The similarity of an amino acid sequence compared with a reference sequence is assessed according to the percentage of amino acid residues which are identical or which differ via conservative substitutions, when the two sequences are aligned so as to obtain the maximum correspondence between them. When only the identical residues are taken into account and the percentage of identical residues is determined, reference is then made to the identity of said amino acid sequence relative to the reference sequence. For the purpose of the present invention, the expression "conservative substitution in the amino acid sequence of a protein" is intended to mean the substitution of one amino acid with another natural or synthetic amino acid which has similar chemical or physical properties (size, charge or polarity), which do not have a deleterious effect on the biological activity of the protein. Thus, two amino acid sequences of a protein are similar when they differ from one another by the substitution of an amino acid, or the deletion and/or insertion of an amino acid or of a small number of amino acids (less than 5) at positions which do not have a deleterious effect on the biological activity of said protein. The percentage similarity or identity can be calculated by those skilled in the art using sequence comparison software, such as, for example, that of the BLAST software series (Altschul et al., NAR, 1997, 25, 3389-3402). The BLAST programs are implemented using the default parameters, on a comparison window consisting of residues 380 to 535 of the amino acid sequence SEQ ID NO: 1.

Unless otherwise indicated, the term "HB-EGF" denotes both the membrane precursor (pro-HB-EGF) and the secreted form of HB-EGF.

The activity of ligand inhibiting HB-EGF refers to the capacity to bind to pro-HB-EGF and to HB-EGF and to the inhibition of various measurable biological phenomena, such as:

the inhibition of the toxic effect of diphtheria toxin on human or simian cells such as Vero cells, the inhibition of the proliferating activity of HB-EGF on cells expressing the ErbB1 and/or ErbB4 subtypes of the EGFR and the growth of which is HB-EGF-dependent, such as a murine lymphoid cell line Ba/F3 transfected with the EGFR gene.

The recombinant protein according to the invention comprises an isolated DTR domain, devoid, at its N- or C-terminal end, of one of the following sequences: (1) the sequence of the T domain or of the C domain and of the T domain of diphtheria toxin, and (2) the sequence of a fusion partner capable of improving the stability of the DTR domain, such as the sequence of gluthatione-S-transferase (GST), or capable of improving the extraction and the purification of the DTR domain from the transformed bacteria, such as the sequence of an immunoglobulin binding domain derived from S. aureus protein A (ZZ domain).

The recombinant protein according to the invention generally comprises an isolated DTR domain which extends from residues 380 to 535 of the sequence SEQ ID NO: 1 and comprises the substitution of one or more, preferably at least two, of the residues Y380, P382, Q387, P388 and/or L390 with a hydrophilic, polar or charged amino acid residue as defined above. However, it may also comprise a slightly shorter isolated DTR domain, the N-terminal end of which is in position 381 to 385 and the C-terminal end of which is in position 531 to 534 of the sequence SEQ ID NO:1. When the N-terminal sequence of DTR is in position 381 or 382, the recombinant protein according to the invention comprises the substitution of at least one of the residues P382, Q387, P388 and/or L390. When the N-terminal sequence of DTR is in position 383, 384 or 385, the recombinant protein according to the invention comprises the substitution of at least one of the residues Q387, P388 and/or L390.

The recombinant protein according to the invention optionally comprises a methionine (M) at its N-ter end and/or additional sequences at the N- and/or C-terminal of the DTR domain. Indeed, the precursor of said recombinant protein comprises an N-terminal methionine which can be cleaved by post-translational modifications, such that it is absent in the mature recombinant protein.

For therapeutic applications, the protein according to the invention consists successively of: (1) a sequence of 1 to 10 amino acids, preferably 1 to 5 amino acids, preferably of 1 or 2 amino acids, the sequence of the precursor and optionally that of the mature protein beginning with a methionine (M), for example an MG sequence, and (2) a mutated DTR domain as defined above. Such a therapeutic protein has a small size, of approximately 145 to 200 amino acids, preferably of approximately 145 to 175 amino acids, preferably of approximately 160 amino acids.

For diagnostic applications, the protein according to the invention is labeled, in particular with a peptide tracer which can be detected by measuring an appropriate signal. The peptide tracer is in particular a tag recognized by an antibody, a fluorescent protein, or a peptide which binds at least one Technetium 99 atom. The label is in the N-ter or C-ter position of the protein, i.e. fused, directly or by means of a peptide spacer, respectively to the N-ter or C-ter end of the DTR domain. Such a protein has a size of approximately 145 to 500 amino acids, preferably of approximately 145 to 300 amino acids, preferably of approximately 145 to 200 amino acids.

The invention encompasses the modified recombinant proteins derived from the previous one by the introduction of any modification at the level of one or more amino acid residue(s), of the peptide bond or of the ends of the recombinant protein, provided that said modified protein retains good affinity and an inhibitory activity with respect to HB-EGF and to pro-HB-EGF. These modifications which are introduced into the proteins by conventional methods known to those skilled in the art include, in a nonlimiting manner: the substitution of an amino acid with a synthetic amino acid (D amino acid or amino acid analog); the addition of a chemical group (lipid, oligosaccharide or polysaccharide) at the level of a reactive function, in particular the side chain R; the modification of the peptide bond (—CO—NH—), in particular via a bond of the retro or retro-inverso type (—NH—CO—) or a bond other than the peptide bond; cyclization; fusion (by genetic engineering) to a peptide or a protein of interest or coupling (via chemical bonding) to a molecule of interest, in particular a labeling agent or tracer which is detectable by measuring a signal.

According to one advantageous embodiment of said protein, it comprises at least one substitution selected from the group consisting of Y380K, Y380E, P382T, Q387E, Q387K, P388T, L390T and L390N.

According to one advantageous arrangement, said substitution(s) is (are) selected from the group consisting of Y380K, Y380E, Q387K, Q387E and L390T. Preferably, said substitution(s) is (are) selected from the group consisting of Y380K, Q387E and L390T.

According to another advantageous arrangement, said protein comprises at least two or three of said substitutions. Preferably, said protein comprises at least the substitutions Y380K and L390T, Y380K and Q387E, Y380E and L390T or Y380E and Q387K, preferably at least the substitutions Y380K and L390T or Y380K and Q387E. For example, said protein comprises one of the following substitution combinations: Y380K and L390T; Y380K, Q387E and L390T; Y380K, Q387E, P388T and L390T; Y380K, Q387E, P382T and L390T; Y380E, Q387K, P382T and L390T. Preferably, it is a protein which comprises or consists of one of the sequences SEQ ID NOs: 2 to 6.

Preferably, said protein comprises at least the substitutions Y380K and L390T. For example, said protein comprises or consists of one of the sequences SEQ ID NOs: 2 to 5.

Even more preferably, said protein comprises the substitutions Y380K, Q387E and L390T. For example, said protein comprises or consists of one of the sequences SEQ ID NOs: 3 to 5, preferably the sequence SEQ ID NO: 3.

According to another advantageous embodiment of said protein, it comprises in addition the substitution A395T. The addition of the substitution produces an additional increase in the yield of soluble protein. Preferably, said protein comprises the sequence SEQ ID NO: 7; this protein called DTR1 comprises the substitutions Y380K, Q387E, L390T and A395T. The HB-EGF-binding affinity of the DTR1 protein is increased by a factor 60 compared with that of CRM197 and by a factor of 130 compared with that of the $DTR_{WT}$ protein solubilized using 0.5% of sarkosyl detergent.

According to yet another advantageous embodiment of said protein, it also comprises at least one of the substitutions F389Y and/or G510A. The addition of one of these substitutions increases the HB-EGF-binding affinity of the DTR protein. In addition, the combination of the two substitutions produces an additional increase in the HB-EGF-binding affinity, compared with the increase obtained with a single substitution. Preferably, said protein comprises or consists of the sequence SEQ ID NO: 8; this protein called DTR3 comprises the substitutions Y380K, Q387E, L390T, A395T, F389Y and G510A. The affinity of the DTR3 protein for HB-EGF is increased by a factor of 5 compared with that of DTR1 and by a factor of 300 compared with that of CRM197.

According to another advantageous embodiment of said protein, it also comprises at least one substitution selected from the group consisting of N399K, V452T, T517E, V483Q, H492E, S494K, T436H and E497D. Said protein advantageously comprises at least 3, preferably at least 5, of said substitutions.

Preferably, said protein comprises the substitutions N399K, V452T, T517E, V483Q, H492E and S494K. These mutations have made it possible to delete 10 of the 26 CD4 T epitopes identified in $DTR_{WT}$. Among these 10 epitopes are 7 of the 9 epitopes predicted as being immunodominant epitopes of $DTR_{WT}$. The capacity of the resulting protein to induce an immune response of CD4 type, i.e. an antibody-producing response, is thus considerably reduced compared with that of DTR$_{WT}$. Notably and unexpectedly, the addition of the six mutations intended to reduce the immunogenicity of DTR has contributed to increasing its affinity for HB-EGF.

Preferably, said protein comprises or consists of the sequence SEQ ID NO: 9; this protein called DTR8 comprises the substitutions Y380K, Q387E, L390T, A395T, F389Y, G510A, N399K, V452T, T517E, V483Q, H492E and S494K. It has a molecular weight of 17458 Da.

The affinity of the DTR8 protein for HB-EGF is increased by a factor of 3 compared with that of DTR3 and by a factor of 1400 compared with that of CRM197. In addition, DTR8 is at least 300 times more effective than CRM197 in terms of binding to secreted HB-EGF and inhibiting the HB-EGF/EGFR pathway.

The antigenicity of the DTR8 protein is greatly reduced compared with that of CRM197. Indeed, most of the antibodies present in adults vaccinated against DT (obligatory vaccination) are directed against the catalytic domain of DT. Surprisingly and unexpectedly, the antigenicity of the DTR8 protein is reduced compared with that of DTR1, and therefore of DTR$_{WT}$.

The protein according to the invention may comprise additional substitutions, in particular of residues located at the surface of the DTR domain, so as to even further reduce its antigenicity.

According to another advantageous embodiment of said protein, it comprises an amino acid sequence which has at least 80% similarity with residues 380 to 535 of the sequence SEQ ID NO: 1, preferably at least 85%, preferably at least 90%. According to one advantageous arrangement of said protein, it comprises an amino acid sequence which has at least 70% identity, preferably at least 80%, 85% or 90% identity, with residues 380 to 535 of the sequence SEQ ID NO: 1.

According to another advantageous embodiment of said protein, it is labeled with a detectable tracer. The means and the techniques for labeling proteins are well known to those skilled in the art and include radioactive, magnetic or fluorescent labeling which can be carried out directly or indirectly. The direct labeling agents are, in particular, radioactive isotopes such as tritium ($^3$H), iodine ($^{125}$I) and technetium ($^{99m}$Tc) or luminescent (radioluminescent, chemoluminescent, bioluminescent, fluorescent or phosphorescent) compounds such as fluorophores, for instance, in a nonlimiting manner, AlexaFluor®, FITC and Cyanine 3, and fluorescent proteins such as GFP and its derivatives. The indirect labeling agents include, in particular, enzymes and epitope tags recognized by a specific antibody. The labeling is in particular carried out by: (1) grafting a fluorophore onto a reactional group such as a reactional amine of a lysine residue, (2) incorporating a reactional group (free cysteine) by chemical synthesis or recombinant production, then using this group to graft a fluorophore, (3) directly incorporating a fluorophore, in the N- or C-terminal position, by chemical synthesis, (4) directly incorporating a fluorescent protein or an enzyme by production of a fusion protein. Such labeled proteins are in particular used as a reagent for the diagnosis, in vitro or in vivo (by imaging), of diseases associated with the activation of the HB-EGF/EGFR pathway or as a tool for studying this activation pathway. The DTR protein can be labeled directly by covalent coupling of technetium ($^{99m}$Tc) or of a fluorescent tracer; the fluorescent tracer is in particular coupled to one of the lysine residues of the DTR protein.

The recombinant protein of the present invention can be produced by means of a method in which an expression vector comprising a polynucleotide encoding said protein, functionally linked to the regulatory elements allowing its expression in the chosen host, is transferred into a host cell which is placed in culture under conditions which allow the expression of said protein. The protein produced is then recovered and purified. The purification methods used are known to those skilled in the art. The recombinant protein obtained can be purified from cell lysates or extracts, or from the culture medium supernatant, by means of methods used individually or in combination, such as fractionation, chromatography methods, or immunoaffinity techniques using specific monoclonal or polyclonal antibodies. The recombinant protein obtained is soluble.

A subject of the present invention is also an isolated polynucleotide encoding said recombinant protein. Said polynucleotide advantageously comprises a coding sequence optimized for expression in the host cell in which the protein of the invention is produced. Preferably, said polynucleotide comprises the sequence SEQ ID NO: 10, 12 or 14 which is optimized for expression in E. coli and encodes respectively the DTR1, DTR3 and DTR8 recombinant protein. The polynucleotide of the invention is a DNA or an RNA prepared using the conventional chemical synthesis or molecular biology methods known to those skilled in the art.

A subject of the present invention is also a recombinant cloning and/or expression vector comprising said polynucleotide. Preferably, said vector is an expression vector comprising said polynucleotide functionally linked to the regulatory sequences which allow the expression of the protein of the invention in the cell host used for the production of said protein (promoter, enhancer, initiation codon (ATG), codon stop, transcription termination signal). The vector, which may be a replicating or integrating vector, in particular a plasmid or a viral vector, is prepared according to the methods commonly used by those skilled in the art.

A subject of the present invention is also a host cell transiently or stably modified with a recombinant vector as defined above. These cells may be obtained by introducing a recombinant vector as defined above into a eukaryotic or prokaryotic host cell using standard methods known to those skilled in the art, such as electroporation. Examples of host cells include, in particular, mammalian cells, insect cells, bacteria such as E. coli and yeasts.

A subject of the present invention is also a pharmaceutical composition comprising at least one recombinant protein or one recombinant expression vector as defined above and a pharmaceutically acceptable vehicle.

The pharmaceutical composition comprises an effective dose of protein or of vector for obtaining a therapeutic effect on diseases associated with activation of the HB-EGF/EGFR pathway, as defined above. Generally, a therapeutically effective amount ranging from approximately 0.1 µg to approximately 100 mg, preferably from 10 µg to 10 mg, can be administered to human adults. The pharmaceutically acceptable vehicles are those conventionally used. The composition is in a galenical form suitable for a chosen administration: injectable sterile solution, powder, tablets, gel capsules, suspension, syrup or suppositories, which are prepared according to standard protocols. The administration may be subcutaneous, intramuscular, intravenous, intradermal, intraperitoneal, oral, sublingual, rectal, vaginal, intranasal, by inhalation or by transdermal application.

The modes of administration, the dosage regimens and the galenical forms of the pharmaceutical compositions according to the invention may be determined in the usual way by those skilled in the art, in particular according to the criteria generally taken into account for establishing a therapeutic treatment suitable for a patient (generally a human individual and optionally a non-human mammal), for instance age, body weight, seriousness of the patient's general condition, tolerance of the treatment, and side effects observed.

A subject of the present invention is also a recombinant protein as defined above, as a medicament.

The present invention also relates to a recombinant protein as defined above, for use in the treatment of diseases associated with activation of the HB-EGF/EGFR pathway.

A subject of the present invention is also the use of a recombinant protein as defined above, for preparing a medicament intended for the treatment of diseases associated with activation of the HB-EGF/EGFR pathway.

A subject of the present invention is also a method for treating diseases associated with activation of the HB-EGF/EGFR pathway, comprising the administration of a pharmaceutical composition as defined above, to an individual. The administration is carried out according to an appropriate mode and an appropriate rate as defined above.

Preferably, said diseases are selected from the group consisting of: rapidly progressive glomerulonephritis (RPGN), cancers, in particular ovarian cancer, endometrial cancer, breast cancer, uterine cancer (uterine adenocarcinoma), bladder cancer, stomach cancer, skin cancer (malignant melanoma), brain cancer (glioblastoma) and lung cancer, vasospasm associated with cerebral contusions, cardiac hypertrophy, smooth muscle cell hyperplasia, pulmonary hypertension, diabetic retinopathies and arterial restenosis.

A subject of the present invention is also the use of a labeled protein as defined above, for the in vitro or in vivo diagnosis of a disease associated with activation of the HB-EGF/EGFR pathway.

The invention also relates to a method for the in vitro diagnosis of a disease associated with activation of the HB-EGF/EGFR pathway, which comprises bringing a biological sample into contact with a labeled protein as defined above, under conditions which allow the formation of a specific complex between said labeled protein and HB-EGF and/or pro-HB-EGF, and detecting said labeled protein/HB-EGF complexes, by any appropriate means.

The biological sample is in particular a biopsy sample (kidney, tumor, smooth muscle, heart, lung, vessels, retina), serum sample or urine sample.

A subject of the present invention is also the use of a labeled protein as defined above, for the detection, in vitro or in vivo, of HB-EGF.

A subject of the present invention is also a method for detecting HB-EGF, in vitro and in vivo, comprising at least the following steps:
bringing cells to be analyzed into contact with a labeled protein as defined above, and
detecting the labeled cells and/or extracellular medium by any appropriate means.

This method makes it possible to determine the tissue expression profile of HB-EGF under physiological or pathological conditions or in response to an endogenous or exogenous stimulus. The detection of HB-EGF, in vivo, in the body of a mammal (cell imaging), in particular in real time, comprises a prior step of administering said protein to said mammal (parenteral injection, oral administration). The detection of HB-EGF in vivo in humans can be used to diagnose a disease associated with activation of the HB-EGF/EGFR pathway.

The labeling of the cells and of the extracellular medium containing HB-EGF is in particular fluorescent or radioactive labeling, or magnetic labeling, detectable by any technique known to those skilled in the art (fluorescence microscopy, flow cytometry, gammagraphy, magnetic resonance imaging).

A subject of the invention is also a kit for carrying out the diagnostic or detection methods as defined above, comprising a labeled protein as defined above.

In addition to the above arrangements, the invention also comprises other arrangements, which will emerge from the following description, which refers to exemplary embodiments of the subject matter of the present invention, with reference to the appended drawings in which.

Figure 7:
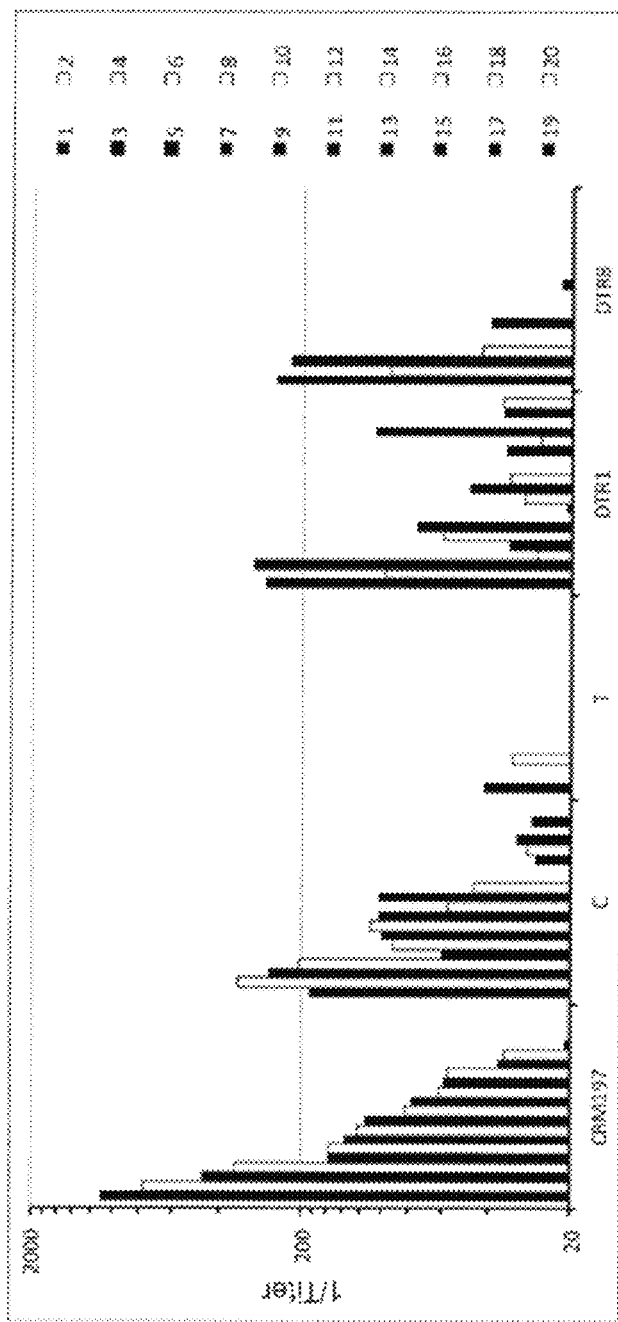

FIG. 7 represents the recognition of the CRM197, diphtheria toxin domain C (C) and domain T (T), DTR1 and DTR8 proteins by the antibodies present in the serum of 20 healthy donors. The titer is defined by the serum dilution which gives a fluorescence signal of 5000 arbitrary units in the ELISA assay, after subtraction of the background noise. A titer ≤20 corresponds to the background noise and therefore to the absence of measurable antibody binding. A titer of 30 was arbitrarily set for distinguishing weak antibody responses from medium or strong responses.

EXAMPLE 1

Materials and Methods

1) Cloning of Genetic Sequences, Expression and Purification of the $DTR_{WT}$ Protein and of its Mutants The genetic sequence encoding the DTR domain of diphtheria toxin, covering the sequence Y380-S535 of the native toxin, was the starting point for this study. All the genetic sequences were synthesized, after optimization for expression in *E. coli*, by the company Geneart according to the previously determined protein sequences. These sequences were cloned into the pET28a(+) vector (Novagen) at the NcoI and SalI restriction sites. The presence of the NcoI site generates the non-native codons M and G corresponding to the N-terminal end of the recombinant protein. The sequence SEQ ID NO: 16 is the optimized nucleotide sequence which encodes the wild-type DTR protein (DTR$_{WT}$) of 158 amino acids, which consists of the residues M and G followed by the residues Y380 to S535 of native diphtheria toxin. The optimized nucleotide sequences encoding the mutant and soluble forms of the DTR protein derive from the sequence SEQ ID NO: 16 by replacement of each codon to be mutated with an optimized codon encoding the mutated amino acid, as indicated in Table I:

TABLE I

List of the optimized codons chosen for the DTR mutations

| Mutation | Wild-type codon | Optimized mutated codon |
|---|---|---|
| Y380K | tac | aaa |
| Y380E | tac | gaa |
| P382T | ccg | acg |
| Q387E | cag | gag |
| Q387K | cag | aag |
| P388T | ccg | acg |
| F389Y | ttt | tat |
| L390T | ctg | acc |
| L390N | ctg | aac |
| H391K | cat | aaa |
| A395T | gcg | acc |
| N399D | aac | gat |
| N399K | aac | aaa |
| V401Q | gtg | cag |
| L427Q | ctg | cag |
| L427N | ctg | aac |
| L427S | ctg | agc |
| T436K | acc | aaa |
| T436H | acc | cat |
| V452T | gtg | acg |
| I457D | att | gat |
| I457E | att | gaa |
| R460T | cgt | acc |
| A463T | gcg | acc |
| A463S | gcg | agc |
| A463E | gcg | gaa |
| A463D | gcg | gat |
| A463G | gcg | ggc |
| Y478T | tat | acc |
| V483D | gtg | gat |
| V483E | gtg | gaa |
| V483H | gtg | cat |
| V483Q | gtg | cag |
| A490G | gcg | ggc |
| H492E | cat | gaa |
| S494K | agc | aaa |
| S496K | agc | aaa |
| E497D | gaa | gat |
| G510A | ggc | gcg |
| G510M | ggc | atg |
| G510Q | ggc | cag |
| G510S | ggc | agc |
| Q515E | cag | gaa |
| T517D | acc | gat |
| T517E | acc | gaa |
| T521R | acc | cgc |
| K522R | aaa | cgc |

The expression of the DTR$_{WT}$ protein was carried out in the *Escherichia coli* BL21(DE3) bacterium in Terrific Broth medium in the presence of 50 µg/ml of kanamycin at 37° C. The induction of the protein is carried out by adding 1 mM of isopropyl β-D-1-thiogalactopyranoside (IPTG). The bacteria were recovered by centrifugation at 5000 g for 45 min and lyzed in a buffer of 20 mM sodium phosphate, 500 mM NaCl, 0.25 mM phenylmethylsulfonyl fluoride (PMSF), lysozyme (0.25 mg/ml), pH 8, by passing them through a Cell Disrupter (Constant Systems). The inclusion bodies containing the protein were solubilized in a solution containing 8 M of urea in 0.1 M Tris-HCl, pH 8. The protein is purified by cation exchange chromatography on a 5 ml HiTrap™ SP column (GE Health Care Life Sciences) according to a buffer gradient between 8 M of urea in 0.1 M Tris-HCl, pH 8, and 8 M of urea, 1 M NaCl in 0.1 M Tris-HCl, pH 8, and then folded by means of dialysis in 2 steps, firstly against a buffer of 20 mM Tris-HCl, 50 mM NaCl, 1 mM cysteine/8 mM cystine, 0.5% sarkosyl, pH 8, and then against a buffer of 20 mM Tris-HCl, 50 mM NaCl, 0.5% sarkosyl, pH 8.

The expression of the mutant and soluble forms of the DTR protein was carried out in the *Escherichia coli* BL21(DE3) bacterium in 2YT medium in the presence of 50 µg/ml of kanamycin. After 2 h 20 min of culture at 37° C., the induction of the protein is carried out by adding 1 mM of IPTG. Then, after 4 h 30 min at 30° C., the bacteria were recovered by centrifugation at 5000 g for 30 min and lyzed in a buffer of 20 mM sodium phosphate, 0.25 mM PMSF, 2 mM MgCl$_2$, supplemented with benzonase (6.25 U/ml), pH 7.8, in a Cell Disrupter (Constant Systems). The protein, which is soluble in the lysis mixture, was purified by cation exchange chromatography on a 5 ml HiTrap™ SP column according to a gradient between 20 mM sodium phosphate, pH 7.8, and 20 mM sodium phosphate, 1 M NaCl, pH 7.8 (GE), and stored at −20° C. in a buffer of 20 mM sodium phosphate, 500 mM NaCl, pH 7.8.

2) Screen for Selecting Soluble Mutants

Three DTR sequence libraries produced by synthesis and cloned into the pET28a(+) plasmid were transfected into the *E. coli* strain BL21(DE3) (Geneart). For each library, clones were subcultured in 2 or 4 96-well plates in culture medium in the presence of a selection antibiotic and of expression inducer (IPTG). After growth, the bacteria were lyzed using a Bugbuster™ solution (0.5× final concentration) (Novagen) with the addition of Lysonase™ (Novagen). After centrifugation of the plates for 20 min at 2700 g at 4° C., the presence of inclusion bodies was evaluated well-by-well through the size of the pellet, and the soluble protein fraction was identified by analysis of the lysis supernatants on a polyacrylamide gel under denaturing conditions and with Coomassie blue staining.

3) Test for Activity of the DTR Proteins by Inhibition of Diphtheria Toxin Toxicity Vero cells (ATCC CCL-81™) were seeded into 96-well Cytostar-T™ scintillating plates (Perkin Elmer) at 50 000 cells per well in DMEM medium (Dulbecco's modified Eagle's minimum essential medium) supplemented with 2 mM of glutamine, 1% of a penicillin/streptomycin solution, 1% of a solution of nonessential amino acids and 10% of fetal calf serum. Variable concentrations of diphtheria toxin (Sigma) were added in duplicates. These conditions were repeated in the presence of the antagonist tested: DTR$_{WT}$, mutant DTR or CRM197 protein (Sigma). After incubation for 22 h at 37° C. in a 5% CO$_2$ atmosphere, the culture medium was replaced with leucine-free medium containing 1 µCi/well of $^{14}$[C]-leucine (GE Health Care Life Sciences). After incubation for 5 h at 37° C. in a 5% CO$_2$ atmosphere, the radioactivity incorporated into the cells was counted by placing the plates, covered with an adhesive film, in a MicroBeta® apparatus (Wallac).

4) Test for Activity of the DTR Proteins by Inhibition of the Proliferating Activity of HB-EGF The test uses a murine lymphoid cell line Ba/F3 (Palacios, R & Steinmetz, M., Cell, 1985, 81, 727-734) transfected in the laboratory with the EGFR gene. This line is dependent on HB-EGF or on amphiregulin for its growth. The cells were seeded into 96-well Nunclon™ plates (Nunc) at 10 000 cells per well in RPMI (Roswell Park Memorial Institute) 1640 medium supplemented with 2 mM of glutamine, 1% of a penicillin/streptomycin solution, 1% of a solution of nonessential amino acids and 10% of fetal calf serum. Variable concentrations of HB-EGF or of amphiregulin were added in duplicate. These conditions were repeated in the presence of the antagonist tested: mutant DTR or CRM197 protein. After incubation for 24 h at 37° C. in a 5% $CO_2$ atmosphere, 1 µCi/well of $^3$[H]-thymidine (GE Health Care Life Sciences) was added to each well. After incubation for 5 h at 37° C. in a 5% $CO_2$ atmosphere, the cells were aspirated on glass fiber filter (filtermat A, Wallac) using a Tomtec® apparatus. After drying of the filters, the latter were placed in a sealed bag in the presence of scintillation fluid and the radioactivity incorporated into the cells was counted in a MicroBeta® apparatus (Wallac).

5) Identification of CD4 T Epitopes of the DTR Protein

The identification of the CD4 T epitopes of the DTR protein is carried out by analysis of the DTR peptides recognized by DTR-specific CD4 T lymphocyte lines, restricted with respect to the HLA-DRB1 molecules which are predominant in caucasian phenotypes. The protocols used are those previously described in application WO 2010/076413 with the exception of the following modifications: (1) the DTR-specific CD4 T lympocyte lines are produced by coculturing of donor CD4 T lymphocytes with autologous mature dendritic cells loaded with a pool of overlapping DTR peptides, and (2) the specificity of the lines produced is analyzed by means of an ELISPOT-IFN-γ assay using autologous peripheral blood mononuclear cells (PBMCs) loaded either with the peptide pool used to produce the CD4 T lymphocyte line, in order to verify the specificity of the line for DTR, or with a peptide of the pool, in order to determine the specificity of each line.

a) Isolation of the CD4 T Lymphocytes from PBMCs

Seven donors of different age and different HLA-DRB1 phenotype were selected such that all of these donors express the 8 HLA-DRB1 molecules which are predominant in caucasian phenotypes (HLA-DR1; HLA-DR3; HLA-DR4; HLA-DR7; HLA-DR11; HLA-DR13; HLA-DR15; HLA-DR8). The CD4 T lymphocytes of each donor were isolated from the peripheral blood mononuclear cells (PBMCs), with a degree of purity greater than 98%, by magnetic sorting on a column using magnetic beads coupled to an anti-CD4 antibody, according to a standard procedure defined by the manufacturer (Myltenyi Biotech).

b) Production and Characterization of the DTR-Specific CD4 T Lymphocyte Lines 25 overlapping peptides of 15 amino acids covering the entire DTR sequence was synthesized (Intavis Bioanalytical Instruments).

TABLE II

| Peptide | Overlapping peptides covering the DTR sequence (SEQ ID NOs: 18 to 42) | | SEQ ID NO: |
|---|---|---|---|
| | Locali-zation | Amino acid sequence | |
| 1 | 378-392 | M G Y S P G H K T Q P F L H D | 18 |
| 2 | 385-399 | K T Q P F L H D G Y A V S W N | 19 |

TABLE II-continued

| Peptide | Overlapping peptides covering the DTR sequence (SEQ ID NOs: 18 to 42) | | SEQ ID NO: |
|---|---|---|---|
| | Locali-zation | Amino acid sequence | |
| 3 | 391-405 | H D G Y A V S W N T V E D S I | 20 |
| 4 | 397-411 | S W N T V E D S I I R T G F Q | 21 |
| 5 | 403-417 | D S I I R T G F Q G E S G H D | 22 |
| 6 | 409-423 | G F Q G E S G H D I K I T A E | 23 |
| 7 | 415-429 | G H D I K I T A E N T P L P I | 24 |
| 8 | 421-435 | T A E N T P L P I A G V L L P | 25 |
| 9 | 427-441 | L P I A G V L L P T I P G K L | 26 |
| 10 | 433-447 | L L P T I P G K L D V N K S K | 27 |
| 11 | 439-453 | G K L D V N K S K T H I S V N | 28 |
| 12 | 445-459 | K S K T H I S V N G R K I R M | 29 |
| 13 | 451-465 | S V N G R K I R M R C R A I D | 30 |
| 14 | 457-471 | I R M R C R A I D G D V T F C | 31 |
| 15 | 463-477 | A I D G D V T F C R P K S P V | 32 |
| 16 | 469-483 | T F C R P K S P V Y V G N G V | 33 |
| 17 | 475-489 | S P V Y V G N G V H A N L H V | 34 |
| 18 | 482-496 | G V H A N L H V A F H R S S S | 35 |
| 19 | 488-502 | H V A F H R S S S E K I H S N | 36 |
| 20 | 494-508 | S S S E K I H S N E I S S D S | 37 |
| 21 | 500-514 | H S N E I S S D S I G V L G Y | 38 |
| 22 | 506-520 | S D S I G V L G Y Q K T V D H | 39 |
| 23 | 512-526 | L G Y Q K T V D H T K V N S K | 40 |
| 24 | 518-532 | V D H T K V N S K L S L F F E | 41 |
| 25 | 521-535 | T K V N S K L S L F F E I K S | 42 |

The peptides were grouped together in 3 pools:

Pool 1: peptides 1 to 8

Pool 2: peptides 9 to 16

Pool 3: peptides 17 to 25.

Each of the pools is used in vitro to repeatedly independently sensitize CD4 T lymphocytes from the donors selected for the study. A minimum of 30 coculture wells are produced per pool of peptides. Firstly, the sensitized CD4 T cells capable of recognizing the peptide pool used during the stimulation, called CD4 T lymphocyte lines, are selected by means of an ELISPOT-IFN-γ assay using autologous PBMCs loaded with the peptide pool, as antigen-presenting cells. Secondly, the peptide(s) specifically recognized by the CD4 T lines selected during the first analysis are identified by means of an ELISPOT-IFN-γ assay using autologous PBMCs separately loaded with each of the peptides of the pool, as antigen-presenting cells. The antigen (isolated peptide or peptide pool) recognition specificity is defined by: (1) a ratio between the number of CD4 T lymphocytes producing IFN-γ in response to the antigen (PBMCs+peptides)

compared with the background noise (absence of the antigen, i.e. PBMCs alone) which is greater than 2, and (2) a minimum number of 30 spots in the presence of antigen once the background noise has been subtracted.

6) Evaluation of the Antigenicity of the DTR Proteins

At each step, the incubations were carried out under one or other of the following three conditions: 1 h at 37° C. or 2 h at 20° C. or 16 h at 4° C. The proteins tested (CRM197, catalytic domain, translocation domain, DTR1 and DTR8) were solubilized at the concentration of $1.7 \times 10^{-8}$ M in the PBS buffer at pH 7.4 so as to be adsorbed onto 96-well Maxisorp™ plates (Nunc). The wells were saturated with a solution of bovine serum albumin (BSA) (Sigma) at 3% in PBS. After 4 washes with a solution of PBS buffer containing 0.05% of Tween 20, the healthy donor sera were incubated in duplicate in the wells after dilution to $\frac{1}{20}^{th}$, $\frac{1}{200}^{th}$ or $\frac{1}{2000}^{th}$ in a PBS buffer containing 0.2% of BSA and 0.05% of Tween 20. After 4 washes with a solution of PBS buffer containing 0.05% de Tween 20, a goat anti-human IgG antibody conjugated to alkaline phosphatase (Sigma) was incubated in the wells after dilution to $\frac{1}{200}^{th}$ in a solution of PBS containing 0.2% of BSA and 0.05% of Tween 20. After 4 washes in a solution of PBS containing 0.05% of Tween 20, the test was visualized by incubation in a 0.1 mM solution of 4-methylumbelliferyl phosphate (Sigma) diluted in the buffer of 50 mM carbonate, 1 mM $MgCl_2$ at pH 9.8 for 30 min at 20° C. The fluorescence of the wells (emission at 450 nm) was measured in a Victor fluorimeter (Wallac) by excitation at 365 nm.

Before being tested, the sera were left to stand at 20° C. for a day, and centrifuged at 10 000 g for 10 min, and then 0.003% of thimerosal was added before storage at 4° C. or at −20° C.

EXAMPLE 2

Improvement of the Solubility of the DTR Protein

The $DTR_{WT}$ protein expressed in *E. coli* accumulates in insoluble inclusion bodies. The protein could be obtained, solubilized and purified only in the presence of 0.5% of sarkosyl or of sodium dodecyl sulfate, which are detergents that are incompatible with therapeutic use at these concentrations. The use of other solubilizing molecules was unsuccessful (Tween-80, sucrose, arginine). The use of chaotropic agents such as urea or guanidine chloride for solubilizing the protein, followed by dialysis against various folding buffers, also does not make it possible to obtain a soluble functional protein. The influence of the DTR truncation site relative to the complete diphtheria toxin sequence was also studied. The DTR forms beginning at residue A379, Y380, S381, P382, G383, H384 or K385 were all insoluble in the absence of detergent.

The strategy used to increase the solubility of the DTR protein consisted in mutating the hydrophobic residues present at the surface of the protein with polar or charged hydrophilic residues. This is because the hydrophobic residues at the surface of a protein are potentially responsible for low solubility and for a tendency to aggregate. The mutations to be introduced were identified on the basis of molecular modeling. The potential effect of the mutations on the structure of the protein is indicated in Table III.

TABLE III

Expected effect of the selected mutations

| Positions | Mutations | Observation regarding structure and interactions |
|---|---|---|
| Y380 | — | Flexible at the end of the N-ter loop, no stable hydrogen bond |
| | Y380E | Ionic bond with K385 |
| | Y380K | Ionic bond with E532 |
| P382 | — | In a type II turn |
| | P382T | |
| Q387 | — | In N-ter loop, no stable hydrogen bond |
| | Q387E | Ionic bond with Y380K |
| P388 | — | In N-ter loop, just before a beta strand |
| | P388T | |
| L390 | — | In a beta strand |
| | L390N | Donor of hydrogen bond for the CO group of the backbone of Y394 |
| | L390T | Beta-branched residue favored |
| A395 | — | In a beta strand |
| | A395T | Beta-branched residue favored |
| N399 | — | In a loop, no stable hydrogen bond |
| | N399D | Ionic bond with K419 |
| N424 | — | In a loop, no stable hydrogen bond |
| | N424D | Ionic bond with N481K |
| | N424E | Ionic bond with N481K |
| | N424K | Ionic bond with E423 or N481E or N481D |
| P426 | — | At the end of a loop |
| | P426T | |
| L427 | — | In a beta strand, Van der Waals contacts with Y394 |
| | L427K | Van der Waals contacts with Y394, donor of hydrogen bond for T425, ionic bond with E423 |
| | L427R | Van der Waals contacts with Y394, donor of hydrogen bond for T425, ionic bond with E423 |
| P428 | — | In a bulge |
| | P428T | |
| P476 | — | In a bulge |
| | P476T | |
| Y478 | — | In a beta strand, Van der Waals contacts with P426, P428, P476 |
| | Y478D | |
| | Y478N | |
| N481 | — | In a loop, no stable hydrogen bond |
| | N481D | Ionic bond with N424K |
| | N481E | Ionic bond with N424K |
| | N481K | Ionic bond with N424E or N424D |
| V483 | — | In a loop |
| | V483T | |

Three DTR DNA sequence libraries were prepared by synthesis (Table IV). Each library contained sequences mutated on 4 or 5 codons chosen according to the molecular modeling data. Each library corresponded to codons mutated in the same region of the coding sequence. The sequences contained partial degeneracies of the codons to be mutated so as to limit the possible mutations to potentially acceptable hydrophilic residues according to the modeling data (1, 2 or 3 possible mutations per position). The possibility of retaining the wild-type codon was maintained, in the case where the position tested cannot tolerate a mutation (Table IV), except for Y380, the N-terminal position of which, which is relatively not very constrained, was considered to be tolerant.

TABLE IV

Combinations of possible mutations expected for each of the three libraries of mutant sequences generated to increase the solubility of the R domain (R1, R2, R3)

| Mutated region | Mutated positions | Possible residues | Library diversity |
|---|---|---|---|
| R1 | Y380 | K/E | 72 |
| | P382 | P/T | |

TABLE IV-continued

Combinations of possible mutations expected for each of the three libraries of mutant sequences generated to increase the solubility of the R domain (R1, R2, R3)

| Mutated region | Mutated positions | Possible residues | Library diversity |
|---|---|---|---|
| R2 | Q387 | Q/E/K | |
| | P388 | P/T | |
| | L390 | L/T/N | |
| | N424 | N/K/D/E | 48 |
| | P426 | P/T | |
| | L427 | L/R/K | |
| | P428 | P/T | |
| R3 | P476 | P/T | 48 |
| | Y478 | Y/N/D | |
| | N481 | N/K/D/E | |
| | V483 | V/T | |

*The diversity indicates the number of combinations of mutations possible for each of the libraries.

Figure 1:
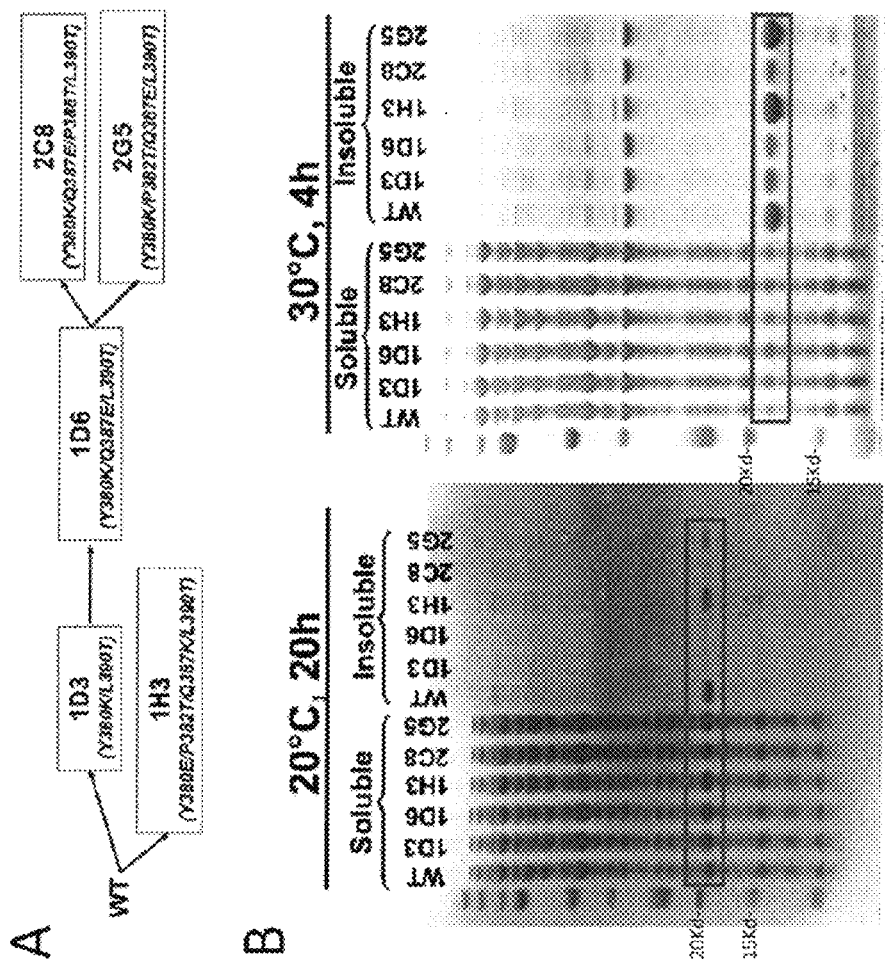
FIG. 1 represents the mutations (A) and the analysis (B) of the soluble and insoluble fractions of the 5 clones selected by screening of the R1 library in order to produce a DTR protein which is more soluble than $DTR_{WT}$. All the clones are soluble; the best clone is the 1 D6 clone.

After transfection of the DNA libraries, the bacterial colonies obtained, each corresponding to a given mutation combination, were analyzed for their possible capacity to produce a soluble mutant form of the DTR protein. For this, 740 clones derived from the three libraries, representing 85% of the expected diversity (41 different clones for each library), were subcultured in 96-well plates, cultured under protein expression induction conditions, centrifuged, and then lyzed in a lysis solution. After centrifugation, the solubility of the proteins expressed by each clone was evaluated by observation for a possible inclusion body pellet at the bottom of the well and by analysis of the supernatant by polyacrylamide gel electrophoresis under denaturing conditions and with Coomassie blue staining (FIG. 1).

The analysis of the colonies resulted in selecting the clones where there was an absence of pellet (pellet corresponding to the inclusion bodies) or a pellet of reduced size and also a large amount of protein in the lysis supernatant. Only the R1 library made it possible to generate clones producing soluble DTR (FIG. 1), there being five of said clones. These clones, called 1D3, 1D6, 2C8, 5G5 and 1H3, comprise the nucleotide sequences encoding the proteins SEQ ID NOs: 2 to 6, respectively. All the clones were soluble after purification according to the method described in Example 1. The 1D6 clone, also called G1, which makes it possible to obtain the largest amount of DTR in soluble form after expression at 30° C., carried the mutations: Y380K/Q387E/L390T.

Figure 2:
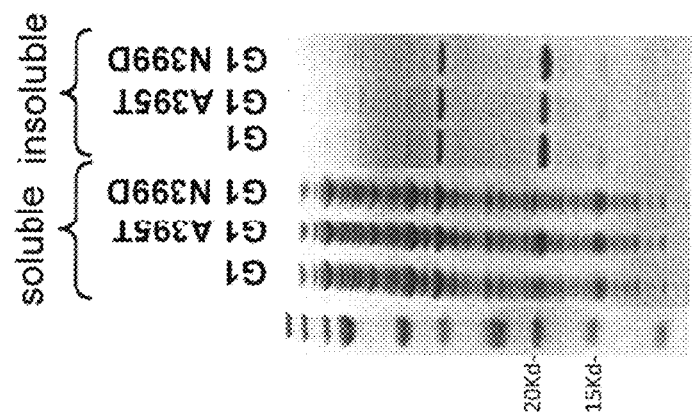
FIG. 2 shows the effects of the A395T and N399D mutations on the solubility of the DTR protein produced by the 1D6 clone (denoted here G1). The best clone contains the A395T mutation.

The modeling approach led to the proposing of two additional mutations, not represented in the R1 library: A395T and N399D. These two mutations were each introduced into the 1D6 clone (or G1 clone) in order to search for an increased solubilizing effect, which was the case for the A395T mutation (FIG. 2).

In total, the most soluble DTR protein, called DTR1 (SEQ ID NO: 7), carries the mutations: Y380K/Q387E/L390T/A395T.

This does not rule out the fact that other DTR mutations may further improve its solubility and its production in E. coli.

Figure 3:
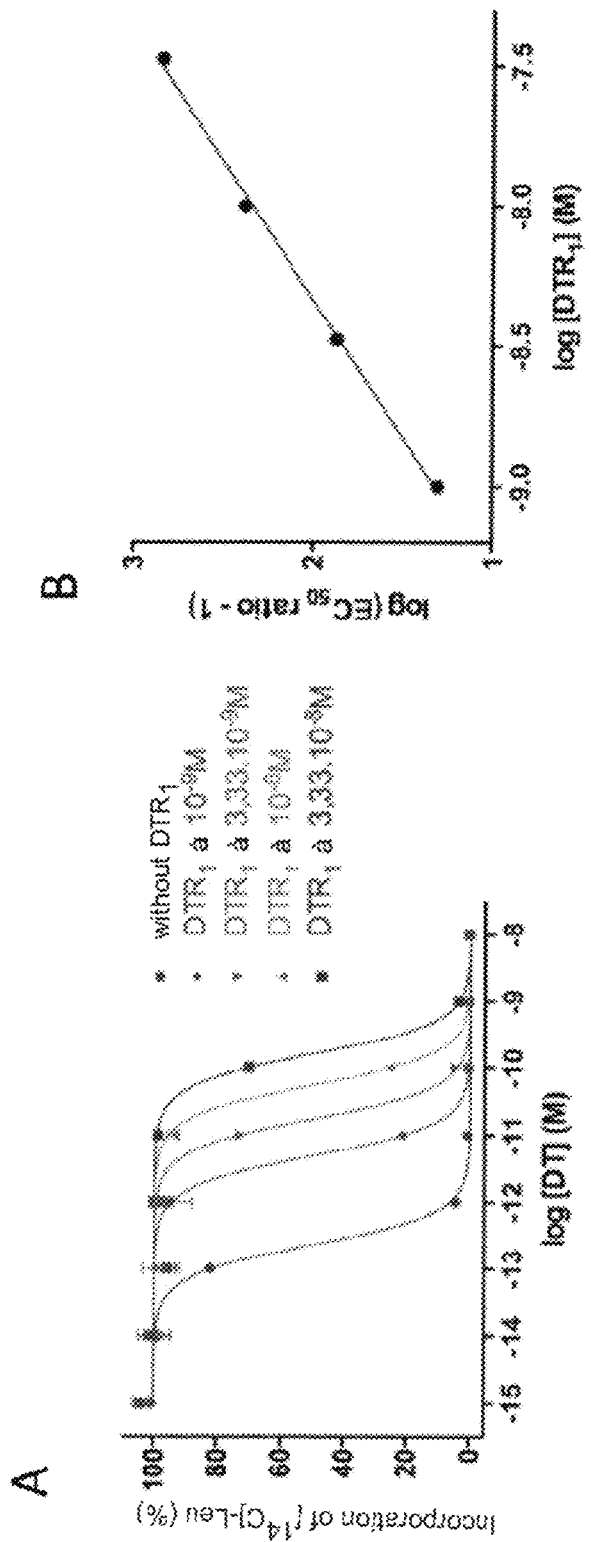
FIG. 3 represents: (A) the inhibition of the toxic effect of increasing doses of diphtheria toxin on Vero cells by increasing doses of DTR1 and (B) the Schild regression for evaluating the Kd of DTR1 for HB-EGF according to the equation log ($EC_{50}$−1)=$K_d$ log (B) where $EC_{50}$ is the concentration of diphtheria toxin which gives 50% toxicity and B is the concentration of inhibitor DTR1.

The HB-EGF-binding activity of the DTR1 protein was evaluated through its capacity to inhibit the poisoning of Vero cells by diphtheria toxin, and therefore the binding of the toxin to pro-HB-EGF. The results show that DTR1 inhibits the poisoning of Vero cells by diphtheria toxin in a dose-dependent manner (FIG. 3). The inhibitory effect of DTR1 was compared with that of CRM197, of the 1D6 clone and of $DTR_{WT}$ solubilized in 0.5% of sarkosyl. The Kd values estimated by Schild regression for the three interactions give the following values:

TABLE V

| Affinity for HB-EGF | |
|---|---|
| Protein | Kd (pM) |
| DTR1 | ~49 |
| Clone 1D6 | ~25 |
| $DTR_{WT}$ (+0.5% sarkosyl) | ~6500 |
| CRM197 | ~3100 |

Biacore experiments in which HB-EGF was immobilized on the chip of the apparatus and DTR1 was injected into the mobile fraction in order to measure the association and dissociation constants made it possible to confirm the estimated Kd of CRM197 and to show a much higher Kd for DTR1. However, the slowness of the dissociation does not allow an accurate measurement of the dissociation constant of DTR1 in Biacore. In the rest of the study, the affinity of the mutants was estimated by cytotoxicity and S child regression.

EXAMPLE 3

Improvement of the Binding Site of the DTR Protein

The structure of diphtheria toxin in interaction with HB-EGF (Louie et al., Mol. Cell., 1997, 1, 67-78) makes it possible to analyze the interface between the two proteins. This structural analysis, coupled with in silico molecular modeling experiments, made it possible to select 10 mutations in the DTR binding site in order to increase the affinity of the protein for HB-EGF. These mutations were intended to increase the enthalpy of the interaction by promoting the formation of hydrogen bonds, of salt bridges and/or of Van der Waals contacts between the two proteins. The potential effect of the selected mutations on the structure of the protein is indicated in Table VI.

TABLE VI

Observations of structural nature regarding the residues selected for increasing the affinity of the DTR protein and expected effect of the mutations

| Positions | Mutations | Observations of structural nature and potential interactions |
|---|---|---|
| F389 | — | In a beta strand, at the edge of the region of interaction with HB-EGF, para-position close to a water molecule of the structured interface and HB-EGF H139 |
| | F389Y | Donor or acceptor of hydrogen bond for a water molecule of the structured interface or HB-EGF H139 |
| H391 | — | In a beta strand, at the edge of the region of interaction with HB-EGF, donor of hydrogen bond for HB-EGF E141 |
| | H391K | Ionic bond with HB-EGF E141 |
| G510 | — | In a beta strand, at the center of the region of interaction with HB-EGF, next to a cavity between DTR and HB-EGF, opposite the CO group of the backbone of HB-EGF C132 |

TABLE VI-continued

Observations of structural nature regarding the residues selected for increasing the affinity of the DTR protein and expected effect of the mutations

| Positions | Mutations | Observations of structural nature and potential interactions |
|---|---|---|
| | G510A | Most conservative change for filling the cavity and increasing Van der Waals contacts |
| | G510M | Flexible hydrophobic side chain for filling the cavity and increasing Van der Waals contacts |
| | G510Q | Donor of hydrogen bond for the CO group of the backbone of HB-EGF C132 and/or acceptor of hydrogen H bond for the NH group of the backbone of HB-EGF C134. |
| | G510S | Small polar side chain for filling the cavity and increasing Van der Waals contacts |
| T521 | — | In a type II turn-like structure, at the edge of the region of interaction with HB-EGF |
| | T521R | Donor of hydrogen bond for the CO group of the backbone of HB-EGF K111 and/or the CO group of the backbone of HB-EGF K113 |
| Q515 | — | In a beta strand, at the edge of the region of interaction with HB-EGF, donor of hydrogen bond for the CO group of the backbone of HB-EGF L127 |
| | Q515E | In an ionic and hydrogen bond network involving K522R, HB-EGF R128, the CO group of the backbone of HB-EGF R128, the CO group of the backbone of HB-EGF L127 |
| K522 | — | In a beta strand, at the edge of the region of interaction with HB-EGF, T517 hydrogen bond donor |
| | K522R | In an ionic and hydrogen bond network involving Q515E, HB-EGF R128, the CO group of the backbone of HB-EGF R128, the CO group of the backbone of HB-EGF L127 |

The mutations were introduced into the DTR1 protein by site-directed mutagenesis (Table VII).

TABLE VII

Mutations for improving the HB-EGF-binding affinity of DTR identified by molecular modeling and tested experimentally

| | |
|---|---|
| F389Y | G510Q |
| H391K | G510S |
| F389Y/H391K | T521R |
| G510A | Q515E/K522R |
| G510M | F389Y/H391K/Q515E/K522R |

Figure 4:
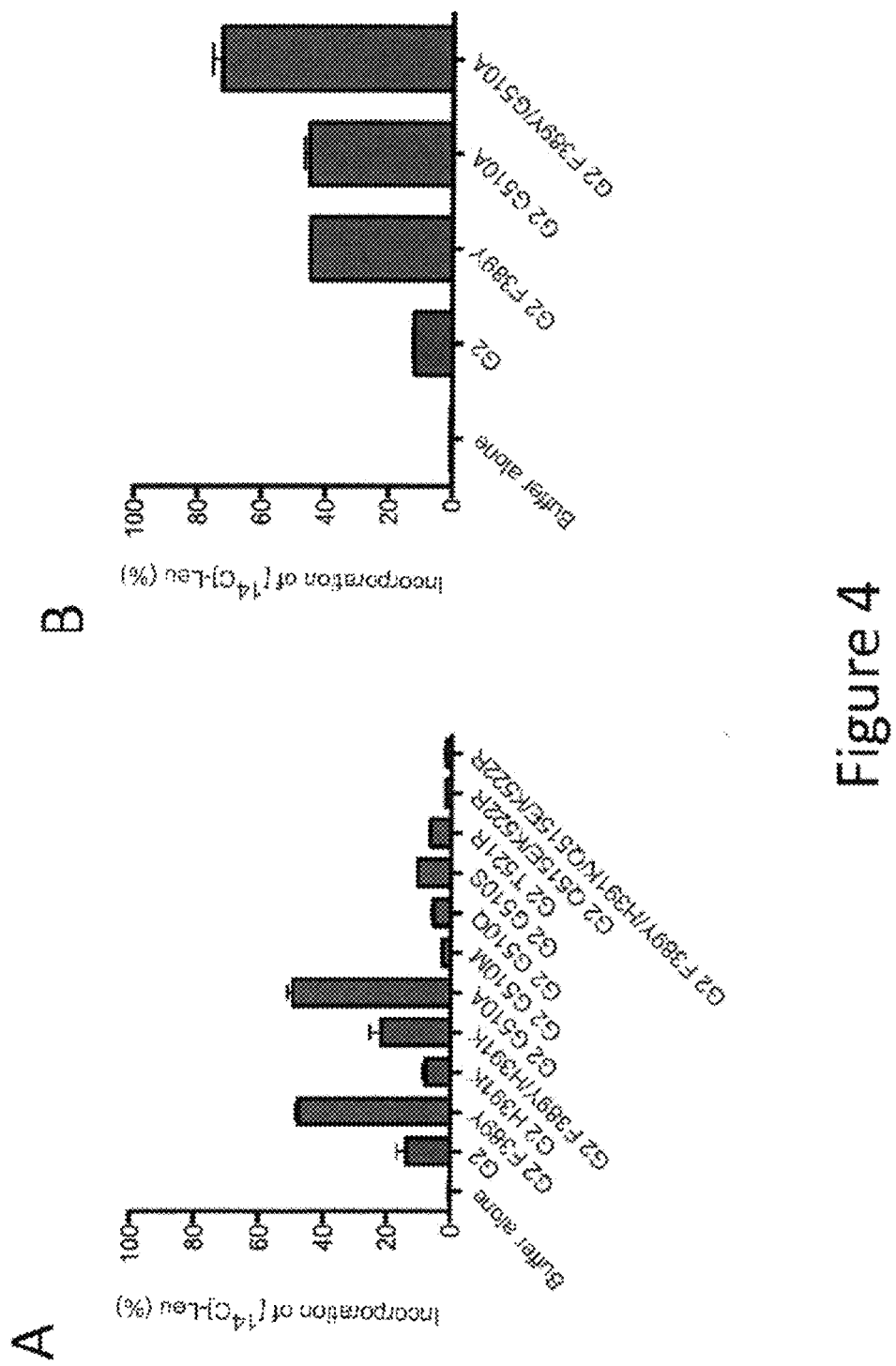
FIG. 4 represents the inhibition of the toxic effect of diphtheria toxin at the concentration of $10^{-11}$ M on Vero cells by each DTR1 mutant (denoted here G2) at a concentration of $10^{-9}$ M.

The proteins were expressed in *E. coli*. They were tested for their capacity to inhibit the binding of diphtheria toxin to pro-HB-EGF according to the cytotoxicity test described in Example 1. FIG. 4A shows the capacity of each mutant to possibly inhibit the toxicity of diphtheria toxin on Vero cells. The results show that only the F389Y and G510A mutants significantly inhibit the toxicity of diphtheria toxin. The introduction of these two mutations into DTR1 leads to a cumulative effect (FIG. 4B).

The most active mutant, corresponding to the DTR1 protein carrying the F389Y and G510A mutations, was called DTR3 (SEQ ID NO: 8). Its HB-EGF-binding affinity was evaluated by the capacity of increasing doses of DTR3 to inhibit the toxic effect of increasing doses of diphtheria toxin on Vero cells as described in Example 2. The Kd estimated by Schild regression from the EC50 values of the inhibition curves is given in Table VIII.

TABLE VIII

Affinity for HB-EGF

| Protein | Kd (pM) |
|---|---|
| DTR3 | ~9.5 |

This value suggests that DTR3 has an affinity for HB-EGF which is at least 300 times greater than CRM197 and 5 times greater than DTR1.

EXAMPLE 4

Decrease in the Immunogenicity of the DTR Protein by Elimination of the Main CD4 T Epitopes The capacity of 25 overlapping peptides covering the entire sequence of $DTR_{WT}$ to activate specific CD4 T lymphocytes was tested by ELISPOT, in vitro immunization experiments using CD4 T lymphocytes and dendritic cells purified from the blood of 7 healthy donors, of different age and of different HLA-DRB 1 phenotype.

The results show that the immune response against the $DTR_{WT}$ protein is directed predominantly against five epitope regions covering 60% of the protein and against which at least 71% of the donors responded, i.e. 5 donors out of 7 studied (Table IX):

the $L_{427}$-$L_{441}$ region (peptide 9) against which specific CD4 T lymphocytes were detected for all of the donors studied with a high magnitude (51 lines among 230 lines screened, i.e. 22%), the $H_{391}$-$Q_{411}$/$S_{451}$-$D_{465}$/$S_{475}$-$N_{502}$ regions (peptides 3-4, 13 and 17-18-19 respectively) against which, overall, specific CD4 T cells were detected for 86% of the donors (i.e. 6 donors/7) with a slightly more moderate magnitude than for the region described above (20 to 30 specific CD4 T lymphocyte lines, i.e. 8.5 to 13%), and the $S_{506}$-$H_{520}$ region (peptide 22) against which specific CD4 T cells were detected for 71% of the donors with a magnitude of 8%.

TABLE IX

Results, by peptide and by donor, for the CD4
T lymphocyte lines specific for the DTR protein

| | | Donors | | | | | | | | |
|---|---|---|---|---|---|---|---|---|---|---|
| | | P668 | P661 | P659 | P663 | P664 | P667 | P658 | | |
| | | | | HLA-DRB1 | | | | | | |
| | | DR3 DR13 | DR1 DR11 | DR13 DR7 | DR4 DR11 | DR1 DR4 | DR8 DR15 | DR3 DR7 | *Total number of CD4 T | Responder |
| | | | | | Age | | | | | |
| Peptides | | 52 | 44 | 29 | 62 | 57 | 44 | 30 | lines | frequency |
| 1 | 378-392 | | | 1 | | | | | 1 | 14 |
| 2 | 385-399 | | 1 | | 4 | | 2 | | 7 | 43 |
| 3 | 391-405 | 1 | | 3 | 2 | 1 | | 4 | 11 | 71 |
| 4 | 397-411 | 1 | | 3 | 1 | 1 | 13 | 8 | 27 | 86 |
| 5 | 403-417 | | | | | 1 | | | 1 | 14 |
| 6 | 409-423 | | 1 | | | 6 | | | 7 | 29 |
| 7 | 415-429 | | | | | | | 1 | 1 | 14 |
| 8 | 421-435 | | 1 | | | | 1 | | 2 | 29 |
| 9 | 427-441 | 3 | 3 | 5 | 3 | 13 | 4 | 20 | 51 | 100 |
| 10 | 433-447 | 1 | | 2 | | 1 | | 18 | 22 | 57 |
| 11 | 439-453 | 2 | 2 | | | | | 1 | 5 | 43 |
| 12 | 445-459 | 9 | | 5 | | | | 3 | 17 | 43 |
| 13 | 451-465 | 9 | | 14 | 1 | 2 | 3 | 1 | 30 | 86 |
| 14 | 457-471 | | | 2 | 1 | | | 1 | 4 | 43 |
| 15 | 463-477 | | | | | | | 10 | 10 | 14 |
| 16 | 469-483 | 2 | | 1 | | | | | 3 | 29 |
| 17 | 475-489 | 7 | 2 | 8 | 5 | | | 1 | 21 | 71 |
| 18-19 | 482-502 | 4 | 1 | 5 | 4 | | 1 | 3 | 18 | 86 |
| 20 | 494-508 | | | 2 | | | | 2 | 4 | 29 |
| 21 | 500-514 | | | 1 | 1 | | | 4 | 6 | 43 |
| 22 | 506-520 | 1 | | 2 | 6 | 4 | 5 | | 18 | 71 |
| 23 | 512-526 | | | | 3 | 2 | | | 5 | 29 |
| 24 | 518-532 | | | 2 | | | 1 | | 3 | 29 |
| 25 | 521-535 | | | 1 | | | | | 1 | 14 |
| | Total | 27 | 16 | 44 | 23 | 28 | 30 | 40 | | |
| | % | 30 | 13 | 49 | 19 | 31 | 33 | 44 | | |

*Total number of CD4 T lymphocyte lines specific for a peptide among the 230 lines screened Since 5 epitope regions were identified, it is possible to envision the mutation of these epitopes in order to reduce their binding to HLA-II molecules. The ProPred server was used to predict, within these five regions of $DTR_{WT}$, the sequences capable of binding the 8 HLA class II alleles which are the most common in the population (Table X). The same analysis applied to the mutated sequences of DTR1 shows that the mutations introduced in order to improve the solubility of DTR reduced the immunogenicity of the protein (epitopes predicted for the region 378-403). Indeed, the epitope predicted to bind DRB1_0301 disappears and one of the epitopes predicted to bind DRB1_0401 experiences an increase in its threshold, that is to say a decrease in its predicted affinity for the HLA molecule.

TABLE X

Prediction of the sequences capable of binding the 8 HLA class II alleles which are the most common (DRB1_0101, DRB1_0301, DRB1_0401, DRB1_0701, DRB1_1101, DRB1_1301, DRB1_1501, DRB5_0101) within the 5 regions identified as immunogenic by means of a CD4 T lymphocyte activation assay. The peptide sequences correspond to the sequences SEQ ID NOs: 43 to 110. The second column of the table gives the region studied. The first column indicates the mutations proposed for inhibiting the binding of the predicted sequences to the HLA class II molecules. The subsequent columns indicate, for each HLA allele considered, the presence or absence of sequence capable of binding this HLA molecule. Each sequence is preceded by a threshold value reflected in the binding strength: 1/2 (strong binding), 3/4 (medium binding), 5/6 (weak binding). The residues in bold correspond to the mutations proposed for abolishing the binding of the sequences to the HLA allele considered.

| Variant | | DRB1_0101 | DRB1_0301 | DRB1_0401 | DRB1_0701 |
|---|---|---|---|---|---|
| | Sequence (378-403) | | | | |
| WT | MGYSPGHKTQPFLHDGYAVSWNTVED (SEQ ID NO: 43) | — | 6: FLHDGYAVS (SEQ ID NO: 45) | 3: FLHDGYAVS (SEQ ID NO: 45) 5: YAVSWNTVE (SEQ ID NO: 46) | — |

TABLE X-continued

Prediction of the sequences capable of binding the 8 HLA class II alleles which are the most common (DRB1_0101, DRB1_0301, DRB1_0401, DRB1_0701, DRB1_1101, DRB1_1301, DRB1_1501, DRB5_0101) within the 5 regions identified as immunogenic by means of a CD4 T lymphocyte activation assay. The peptide sequences correspond to the sequences SEQ ID NOs: 43 to 110. The second column of the table gives the region studied. The first column indicates the mutations proposed for inhibiting the binding of the predicted sequences to the HLA class II molecules. The subsequent columns indicate, for each HLA allele considered, the presence or absence of sequence capable of binding this HLA molecule. Each sequence is preceded by a threshold value reflected in the binding strength: 1/2 (strong binding), 3/4 (medium binding), 5/6 (weak binding). The residues in bold correspond to the mutations proposed for abolishing the binding of the sequences to the HLA allele considered.

| Mutation | Peptide | DRB1_0101 | DRB1_0301 | DRB1_0401 | DRB1_0701 | DRB1_1101 | DRB1_1301 | DRB1_1501 | DRB5_0101 |
|---|---|---|---|---|---|---|---|---|---|
| DTR1 | MGKSPGHKTEPFTHDGYTVSWNTVED (SEQ ID NO: 44) | – | – | – | – | 5: FTHDGYTVS (SEQ ID NO: 47) 5: YTVSWNTVE (SEQ ID NO: 48) | – | | |

Sequence (391-411)

| Mutation | Peptide | DRB1_0101 | DRB1_0301 | DRB1_0401 | DRB1_0701 | DRB1_1101 | DRB1_1301 | DRB1_1501 | DRB5_0101 |
|---|---|---|---|---|---|---|---|---|---|
| DTR1 | HDGYTVSWNTVEDSIIRTGFQ (SEQ ID NO: 49) | – | – | 4: VSWNTVEDS (SEQ ID NO: 53) 5: YTVSWNTVE (SEQ ID NO: 54) | 6: WNTVEDSII (SEQ ID NO: 55) | | | | |
| N399K | HDGYTVSWKTVEDSIITGFQ (SEQ ID NO: 50) | – | – | – | 5: WKTVEDSII (SEQ ID NO: 56) | | | | |
| V401Q | HDGYTVSWNTQEDSIIRTGFQ (SEQ ID NO: 51) | – | – | 5: YTVSWNTQE (SEQ ID NO: 58) | – | | | | |
| N399K V401Q | HDGYTVSWKTQEDSIIRTGFQ (SEQ ID NO: 52) | – | – | – | – | | | | |

Sequence (427-441)

| Mutation | Peptide | DRB1_0101 | DRB1_0301 | DRB1_0401 | DRB1_0701 | DRB1_1101 | DRB1_1301 | DRB1_1501 | DRB5_0101 |
|---|---|---|---|---|---|---|---|---|---|
| DTR1 | LPIAGVLLPTIPGKL (SEQ ID NO: 59) | – | 6: VLLPTIPGK (SEQ ID NO: 63) | – | 3: LLPTIPGKL (SEQ ID NO: 65) | | | | |
| L427Q | QPIAGVLLPTIPGKL (SEQ ID NO: 60) | – | 6: VLLPTIPGK (SEQ ID NO: 63) | – | 3: LLPTIPGKL (SEQ ID NO: 65) | | | | |
| T436K | LPIAGVLLPKIPGKL (SEQ ID NO: 61) | – | 6: VLLPKIPGK (SEQ ID NO: 64) | – | – | | | | |
| L427Q T436K | QPIAGVLLPKIPGKL (SEQ ID NO: 62) | – | 6: VLLPKIPGK (SEQ ID NO: 64) | – | – | | | | |

Sequence (451-465)

| Mutation | Peptide | DRB1_0101 | DRB1_0301 | DRB1_0401 | DRB1_0701 | DRB1_1101 | DRB1_1301 | DRB1_1501 | DRB5_0101 |
|---|---|---|---|---|---|---|---|---|---|
| DTR1 | SVNGRKIRMRCRAID (SEQ ID NO: 67) | – | 3: IRMRCRAID (SEQ ID NO: 74) | – | – | | | | |
| I457D | SVNGRKDRMRCRAID (SEQ ID NO: 68) | – | – | – | – | | | | |
| I457E | SVNGRKERMRCRAID (SEQ ID NO: 69) | – | – | – | – | | | | |
| V452T | STNGRKIRMRCRAID (SEQ ID NO: 70) | – | 3: IRMRCRAID (SEQ ID NO: 74) | – | – | | | | |
| R460T | SVNGRKIRMTCRAID (SEQ ID NO: 71) | – | 3: IRMTCRAID (SEQ ID NO: 75) | – | – | | | | |
| A463D | SVNGRKIRMRCRDID (SEQ ID NO: 72) | – | 5: IRMRCRDID (SEQ ID NO: 76) | – | – | | | | |
| V452T R460T A463D | STNGRKIRMTCRDID (SEQ ID NO: 73) | – | 5: IRMTCRDID (SEQ ID NO: 77) | – | – | | | | |

Sequence (475-502)

| Mutation | Peptide | DRB1_0101 | DRB1_0301 | DRB1_0401 | DRB1_0701 | DRB1_1101 | DRB1_1301 | DRB1_1501 | DRB5_0101 |
|---|---|---|---|---|---|---|---|---|---|
| DTR1 | SPVYVGNGVHANLHVAFHRSSSEKIHSN (SEQ ID NO: 80) | 3: YVGNGVHAN (SEQ ID NO: 91) 3: FHRSSSEKI (SEQ ID NO: 92) 4: VYVGNGVHA (SEQ ID NO: 93) | – | 1: YVGNGVHAN (SEQ ID NO: 91) 1: FHRSSSEKI (SEQ ID NO: 92) | 1: YVGNGVHAN (SEQ ID NO: 91) 1: FHRSSSEKI (SEQ ID NO: 92) | | | | |
| Y478T | SPVTVGNGVHANLHVAFHRSSSEKIHSN (SEQ ID NO: 81) | 3: FHRSSSEKI (SEQ ID NO: 92) | – | 1: FHRSSSEKI (SEQ ID NO: 92) | 1: FHRSSSEKI (SEQ ID NO: 92) | | | | |
| V483D | SPVYVGNGDHANLHVAFHRSSSEKIHSN (SEQ ID NO: 82) | 3: FHRSSSEKI (SEQ ID NO: 92) | – | 1: FHRSSSEKI (SEQ ID NO: 92) 5: YVGNGDHAN (SEQ ID NO: 95) | 1: FHRSSSEKI (SEQ ID NO: 92) | | | | |
| V483E | SPVYVGNGEHANLHVAFHRSSSEKIHSN (SEQ ID NO: 83) | 3: FHRSSSEKI (SEQ ID NO: 92) | – | 1: FHRSSSEKI (SEQ ID NO: 92) | 1: FHRSSSEKI (SEQ ID NO: 92) | | | | |
| V483H | SPVYVGNGHHANLHVAFHRSSSEKIHSN (SEQ ID NO: 84) | 3: FHRSSSEKI (SEQ ID NO: 92) 5: VYVGNGHHA (SEQ ID NO: 96) | – | 1: FHRSSSEKI (SEQ ID NO: 92) | 1: FHRSSSEKI (SEQ ID NO: 92) | | | | |

TABLE X-continued

Prediction of the sequences capable of binding the 8 HLA class II alleles which are the most common (DRB1_0101, DRB1_0301, DRB1_0401, DRB1_0701, DRB1_1101, DRB1_1301, DRB1_1501, DRB5_0101) within the 5 regions identified as immunogenic by means of a CD4 T lymphocyte activation assay. The peptide sequences correspond to the sequences SEQ ID NOs: 43 to 110. The second column of the table gives the region studied. The first column indicates the mutations proposed for inhibiting the binding of the predicted sequences to the HLA class II molecules. The subsequent columns indicate, for each HLA allele considered, the presence or absence of s

TABLE X-continued

Prediction of the sequences capable of binding the 8 HLA class II alleles which are the most common (DRB1_0101, DRB1_0301, DRB1_0401, DRB1_0701, DRB1_1101, DRB1_1301, DRB1_1501, DRB5_0101) within the 5 regions identified as immunogenic by means of a CD4 T lymphocyte activation assay. The peptide sequences correspond to the sequences SEQ ID NOs: 43 to 110. The second column of the table gives the region studied. The first column indicates the mutations proposed for inhibiting the binding of the predicted sequences to the HLA class II molecules. The subsequent columns indicate, for each HLA allele considered, the presence or absence of sequence capable of binding this HLA molecule. Each sequence is preceded by a threshold value reflected in the binding strength: 1/2 (strong binding), 3/4 (medium binding), 5/6 (weak binding). The residues in bold correspond to the mutations proposed for abolishing the binding of the sequences to the HLA allele considered.

| | | | | | |
|---|---|---|---|---|---|
| T436K | LPIAGVLLPKIPGKL (SEQ ID NO: 61) | 3: LPIAGVLLP (SEQ ID NO: 66) | 4: LPIAGVLLP (SEQ ID NO: 66) | — | — |
| L427Q T436K | QPIAGVLLPKIPGKL (SEQ ID NO: 62) | — | — | — | — |
| | Sequence (451-465) | | | | |
| DTR1 | SVNGRKIRMRCRAID (SEQ ID NO: 67) | 3: IRMRCRAID (SEQ ID NO: 74) | 1: VNGRKIRMR (SEQ ID NO: 78) 1: IRMRCRAID (SEQ ID NO: 74) | 4: IRMRCRAID (SEQ ID NO: 74) | — |
| I457D | SVNGRKDRMRCRAID (SEQ ID NO: 68) | — | — | — | — |
| I457E | SVNGRKERMRCRAID (SEQ ID NO: 69) | — | — | — | — |
| V452T | STNGRKIRMRCRAID (SEQ ID NO: 70) | 3: IRMRCRAID (SEQ ID NO: 74) | 1: IRMRCRAID (SEQ ID NO: 74) | 4: IRMRCRAID (SEQ ID NO: 74) | — |
| R460T | SVNGRKIRMTCRAID (SEQ ID NO: 71) | 3: IRMTCRAID (SEQ ID NO: 75) | 3: VNGRKIRMT (SEQ ID NO: 79) 3: IRMTCRAID (SEQ ID NO: 75) | 6: IRMTCRAID (SEQ ID NO: 75) | — |
| A463D | SVNGRKIRMRCRDID (SEQ ID NO: 72) | — | 1: VNGRKIRMR (SEQ ID NO: 78) 3: IRMRCRDID (SEQ ID NO: 76) | — | — |
| V452T R460T A463D | STNGRKIRMTCRDID (SEQ ID NO: 74) | — | — | — | — |
| | Sequence (475-502) | | | | |
| DTR1 | SPVYVGNGVHANLHVAFHRSSSEKIHSN (SEQ ID NO: 80) | 2: YVGNGVHAN (SEQ ID NO: 91) 5: LHVAFHRSS (SEQ ID NO: 94) | 1: LHVAFHRSS (SEQ ID NO: 94) 4: YVGNGVHAN (SEQ ID NO: 91) | — | — |
| Y478T | SPVTVGNGVHANLHVAFHRSSSEKIHSN (SEQ ID NO: 81) | 5: LHVAFHRSS (SEQ ID NO: 94) | 1: LHVAFHRSS (SEQ ID NO: 94) | — | — |
| V483D | SPVYVGNGDHANLHVAFHRSSSEKIHSN (SEQ ID NO: 82) | 5: LHVAFHRSS (SEQ ID NO: 94) | 1: LHVAFHRSS (SEQ ID NO: 94) | — | — |
| V483E | SPVYVGNGEHANLHVAFHRSSSEKIHSN (SEQ ID NO: 83) | 5: LHVAFHRSS (SEQ ID NO: 94) | 1: LHVAFHRSS (SEQ ID NO: 94) | — | — |
| V483H | SPVYVGNGHHANLHVAFHRSSSEKIHSN (SEQ ID NO: 84) | 5: VYVGNGHHA (SEQ ID NO: 96) 5: LHVAFHRSS (SEQ ID NO: 94) | 1: LHVAFHRSS (SEQ ID NO: 94) | 6: VYVGNGHHA (SEQ ID NO: 96) | — |
| V483Q | SPVYVGNGQHANLHVAFHRSSSEKIHSN (SEQ ID NO: 85) | 5: YVGNGQHAN (SEQ ID NO: 98) 5: LHVAFHRSS (SEQ ID NO: 94) | 1: LHVAFHRSS (SEQ ID NO: 94) | — | — |
| A490G | APVYVGNGVHANLHVGFHRSSSEKIHSN (SEQ ID NO: 86) | 2: YVGNGVHAN (SEQ ID NO: 91) | 4: YVGNGVHAN (SEQ ID NO: 91) 5: LHVGFHRSS (SEQ ID NO: 99) | — | — |
| H492E | SPVYVGNGVHANLHVAFERSSSEKIHSN (SEQ ID NO: 87) | 2: YVGNGVHAN (SEQ ID NO: 91) | 4: YVGNGVHAN (SEQ ID NO: 91) 5: LHVAFERSS (SEQ ID NO: 101) | — | — |
| S494K | SPVYVGNGVHANLHVAFHRKSSEKIHSN (SEQ ID NO: 88) | 2: YVGNGVHAN (SEQ ID NO: 91) 5: LHVAFHRKS (SEQ ID NO: 103) | 1: LHVAFHRKS (SEQ ID NO: 103) 4: YVGNGVHAN (SEQ ID NO: 91) 4: VAFHRKSSE (SEQ ID NO: 104) | — | — |

TABLE X-continued

Prediction of the sequences capable of binding the 8 HLA class II alleles which are the most common (DRB1_0101, DRB1_0301, DRB1_0401, DRB1_0701, DRB1_1101, DRB1_1301, DRB1_1501, DRB5_0101) within the 5 regions identified as immunogenic by means of a CD4 T lymphocyte activation assay. The peptide sequences correspond to the sequences SEQ ID NOs: 43 to 110. The second column of the table gives the region studied. The first column indicates the mutations proposed for inhibiting the binding of the predicted sequences to the HLA class II molecules. The subsequent columns indicate, for each HLA allele considered, the presence or absence of sequence capable of binding this HLA molecule. Each sequence is preceded by a threshold value reflected in the binding strength: 1/2 (strong binding), 3/4 (medium binding), 5/6 (weak binding). The residues in bold correspond to the mutations proposed for abolishing the binding of the sequences to the HLA allele considered.

| | | | | | |
|---|---|---|---|---|---|
| S496K | SPVYVGNGVHANLHVAFHRSSKEKIHSN (SEQ ID NO: 89) | 2: YVGNGVHAN (SEQ ID NO: 91)<br>5: LHVAFHRSS (SEQ ID NO: 94)<br>5: FHRSSKEKI (SEQ ID NO: 105) | 1: LHVAFHRSS (SEQ ID NO: 94)<br>4: YVGNGVHAN (SEQ ID NO: 91) | — | — |
| Y478T<br>A490G<br>H492E<br>S494K<br>S496K | SPVTVGNGVHANLHVGFERKSKEKIHSN (SEQ ID NO: 90) | — | — | — | — |
| | Sequence (506-520) | | | | |
| DTR1 | SDSIGVLGYQKTVDH (SEQ ID NO: 106) | 6: LGYQKTVDH (SEQ ID NO: 109) | 5: LGYQKTVDH (SEQ ID NO: 109) | — | — |
| T517D | SDSIGVLGYQKDVDH (SEQ ID NO: 107) | — | — | — | — |
| T517E | SDSIGVLGYQKEVDH (SEQ ID NO: 108) | — | — | — | — |

The prediction of the anchoring residues of the sequences predicted to bind the HLA class II molecules made it possible to propose a series of mutations indicated in bold in Table X, intended to eliminate potential T epitopes. The mutations were chosen so as to avoid potential destabilization of the protein, which was tested in silico by molecular modeling. Any mutation affecting the HB-EGF-binding site was excluded. The potential effect of the proposed mutations on the structure of the protein is indicated in Table XI.

TABLE XI

Observations of structural nature regarding the residues selected for eliminating CD4 T epitopes of the DTR protein and expected effect of the mutations

| Positions | Mutations | Observations of structural nature and potential interactions |
|---|---|---|
| N399 | — | Exposed to the solvent, in a loop, no stable hydrogen bond |
| | N399K | Ionic bond with D417 and donor of hydrogen bond for the CO group of the backbone of N486 |
| V401 | — | Exposed to the solvent, in a type I turn |
| | V401Q | Acceptor of hydrogen bond for K385 |
| L427 | — | Partially buried, in a beta strand, Van der Waals contacts with Y394 |
| | L427Q | Donor of hydrogen bond for the CO group of the backbone of D392, hydrocarbon-based side chain establishing Van der Waals contacts with Y394 |
| T436 | — | Partially buried, in a loop, donor of hydrogen bond for the CO group of the backbone of G466, Van der Waals contacts with V443 |
| | T436H | Acceptor of hydrogen bond for T469, Van der Waals contacts with V443 |
| | T436K | Ionic bond with A463D |
| I457 | — | Largely buried; in a beta strand; Van der Waals contacts with I450, V452, P473, V477 |
| | I457D | Acceptor of hydrogen bond for S475, the NH group of the backbone of S475, the NH group of the backbone of K474 |
| | I457E | Acceptor of hydrogen bond for S475, the NH group of the backbone of S475, the NH group of the backbone of K474, or the NH group of the backbone of V452 |
| V452 | — | Partially buried, in a beta strand, Van der Waals contacts by a methyl group of the side chain with I450, I457, V477 |
| | V452T | Van der Waals contacts by the methyl group of the side chain with I450, I457, V477 |
| A463 | — | Exposed to the solvent, in a beta strand |
| | A463D | Ionic bond with T436K |

TABLE XI-continued

Observations of structural nature regarding the residues selected for eliminating CD4 T epitopes of the DTR protein and expected effect of the mutations

| Positions | Mutations | Observations of structural nature and potential interactions |
|---|---|---|
| R460 | — | Exposed to the solvent, in a beta strand, is part of a basic patch containing other arginines potentially interacting with heparan sulfate groups bonded to the plasma membrane, close to HB-EGF, donor of hydrogen bond for the CO group of the backbone of P473 |
|  | R460T | Beta-branched residue |
| Y478 | — | Exposed to the solvent, in a beta strand, Van der Waals contacts with P426, P428, P476 |
|  | Y478T | Beta-branched residue |
| V483 | — | Exposed to the solvent, in a loop |
|  | V483D |  |
|  | V483E | Acceptor of hydrogen bond for V452T, N453 |
|  | V483H | Donor of hydrogen bond for the CO group of the backbone of Y478 |
|  | V483Q | Acceptor or donor of hydrogen bond for V452T, donor of hydrogen bond for the CO group of the backbone of Y478 |
| A490 | — | Partially buried, in a beta strand |
|  | A490G |  |
| H492 | — | Exposed to the solvent, in a beta strand, acceptor or donor of hydrogen bond for S494 |
|  | H492E | Ionic bond with S494K |
| S494 | — | Exposed to the solvent, in a loop, acceptor of hydrogen bond for H492 |
|  | S494K | Ionic bond with H492E |
| S496 | — | Exposed to the solvent, in a loop |
|  | S496K | Donor of hydrogend bond for Q411 |
| T517 | — | Exposed to the solvent, in a beta strand, acceptor of hydrogen bond for K522 |
|  | T517D | Ionic bond with K522 |
|  | T517E | Ionic bond with K522 |

The mutations indicated in Table XII were introduced individually, or sometimes in combination, into the sequence of the DTR3 protein, according to the modeling data, then gradually accumulated when they altered neither the production of the recombinant protein nor its biological activity. The biological activity of the mutants was tested by inhibition of the toxicity of diphtheria toxin on Vero cells.

TABLE XII

Mutations introduced into DTR3 in order to eliminate CD4 T epitopes

| | | |
|---|---|---|
| N399K | A463S | H492E |
| V401Q | A463E | S494K |
| L427Q | A463D | S496K |
| L427N | A463G | H492E/S494K |
| L427S | T436K/A463D | H492E/S496K |
| T436K | V452T/R460T/A463D | S494K/S496K |
| T436H | Y478T | H492E/S494K/S496K |

TABLE XII-continued

Mutations introduced into DTR3 in order to eliminate CD4 T epitopes

| | | |
|---|---|---|
| V452T | V483D | E497D |
| I457D | V483E | T436H/E497D |
| I457E | V483H | T517D |
| R460T | V483Q | T517E |
| A463T | A490G |  |

* In bold, the mutations which do not significantly affect the expression and the activity of the protein, which were therefore retained.

These experiments made it possible to successively retain the following mutations: N399K, V452T, T517E, V483Q, H492E, S494K, T436H and E497D.

The protein derived from DTR3 and accumulating the N399K, V452T, T517E, V483Q, H492E and S494K mutations is called DTR8 (SEQ ID NO: 9); it has an MW of 17458 Da. These mutations made it possible to eliminate 10 of the 26 CD4 T epitopes identified in $DTR_{WT}$ (Table XIII).

TABLE XIII

Comparison of the number and of the strength of the binding to HLA II of the CD4 T epitopes between $DTR_{WT}$ and DTR8

| DTR | Strength of binding to HLA II | Threshold value reflecting the binding strength | CD4 T epitopes | | | | | Total number |
|---|---|---|---|---|---|---|---|---|
| | | | 391-411 | 427-441 | 451-465 | 475-502 | 506-520 | |
| $DTR_{WT}$ | Strong | 1 | 0 | 0 | 2 | 4 | 1 | 7 |
|  |  | 2 | 0 | 1 | 0 | 1 | 0 | 2 |
|  | Medium | 3 | 0 | 2 | 2 | 2 | 0 | 6 |
|  |  | 4 | 1 | 1 | 1 | 2 | 0 | 5 |

TABLE XIII-continued

Comparison of the number and of the strength of the binding to HLA II of the CD4 T epitopes between $DTR_{WT}$ and DTR8

| DTR | Strength of binding to HLA II | Threshold value reflecting the binding strength | 391-411 | 427-441 | 451-465 | 475-502 | 506-520 | Total number |
|---|---|---|---|---|---|---|---|---|
|  | Weak | 5 | 1 | 0 | 0 | 1 | 1 | 3 |
|  |  | 6 | 1 | 1 | 0 | 0 | 1 | 3 |
|  |  | Total | 3 | 5 | 5 | 10 | 3 | 26 |
| DTR8 | Strong | 1 | 0 | 0 | 1 | 0 | 0 | 1 |
|  |  | 2 | 0 | 1 | 0 | 0 | 0 | 1 |
|  | Medium | 3 | 0 | 2 | 2 | 1 | 0 | 5 |
|  |  | 4 | 0 | 1 | 1 | 0 | 0 | 2 |
|  | Weak | 5 | 1 | 0 | 0 | 3 | 0 | 4 |
|  |  | 6 | 1 | 1 | 0 | 1 | 0 | 3 |
|  |  | Total | 2 | 5 | 4 | 5 | 0 | 16 |

Among these 10 epitopes are 7 of the 9 epitopes predicted as being immunodominant epitopes of $DTR_{WT}$. The capacity of the resulting protein, DTR8, to induce a CD4-type immune response, i.e. producing antibodies, is thus considerably reduced compared with that of $DTR_{WT}$ in its wild-type form.

Figure 5:
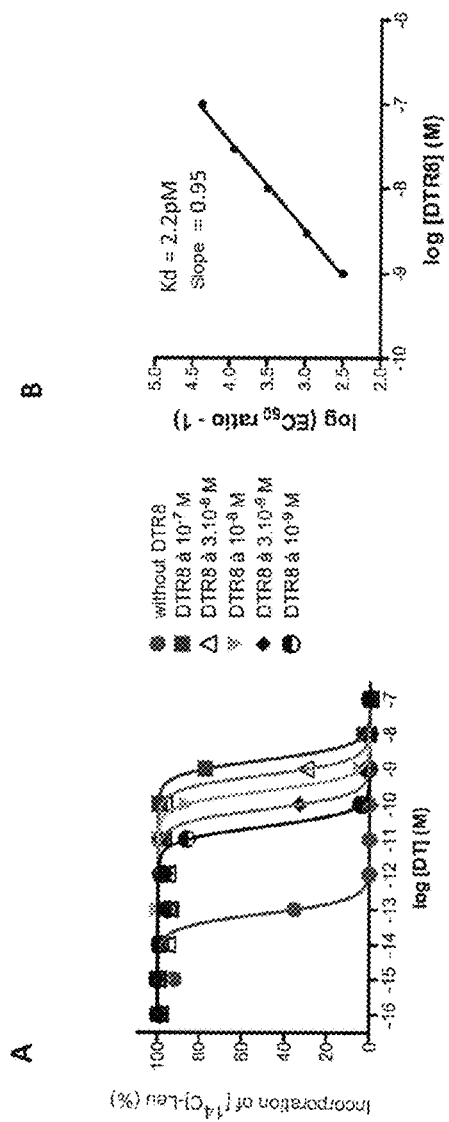
FIG. 5 represents: (A) the inhibition of the toxic effect of increasing doses of diphtheria toxin on Vero cells by increasing doses of DTR8 and (B): the Schild regression for evaluating the Kd of DTR8 for HB-EGF according to the equation log ($EC_{50}$−1)=$K_d$ log (B) where $EC_{50}$ is the concentration of diphtheria toxin which gives 50% toxicity and B is the concentration of inhibitor DTR8.

DTR8 contains six more mutations than DTR3. Since any mutation or mutation combination is capable of impairing the function of a protein, it is necessary to evaluate the effect of these additional mutations on the DTR binding affinity for HB-EGF. The HB-EGF-binding activity of the DTR8 protein was evaluated through its capacity to inhibit the poisoning of Vero cells by diphtheria toxin, and therefore the binding of the toxin to pro-HB-EGF. The results (FIG. 5) show that DTR8 inhibits the poisoning of Vero cells by diphtheria toxin in a dose-dependent manner. The inhibitory effect of DTR8 was compared with that of CRM197, $DTR_{WT}$ solubilized in 0.5% of sarkosyl, DTR3 and DTR1 (FIG. 3). The Kd values estimated by Schild regression for the four interactions give the following values (Table XIV).

TABLE XIV

Affinity of the proteins for HB-EGF

| Protein | Kd (pM) |
|---|---|
| DTR8 | 2.2 |
| DTR3 | 9.5 |
| DTR1 | 49 |
| $DTR_{WT}$ (+0.5% sarkosyl) | 6500 |
| CRM197 | 3100 |

Notably and unexpectedly, the addition of the six mutations intended to reduce the immunogenicity of DTR contributed to increasing its affinity for HB-EGF. Overall, DTR8 has approximately 1400 times more affinity for HB-EGF than CRM197.

Figure 6:
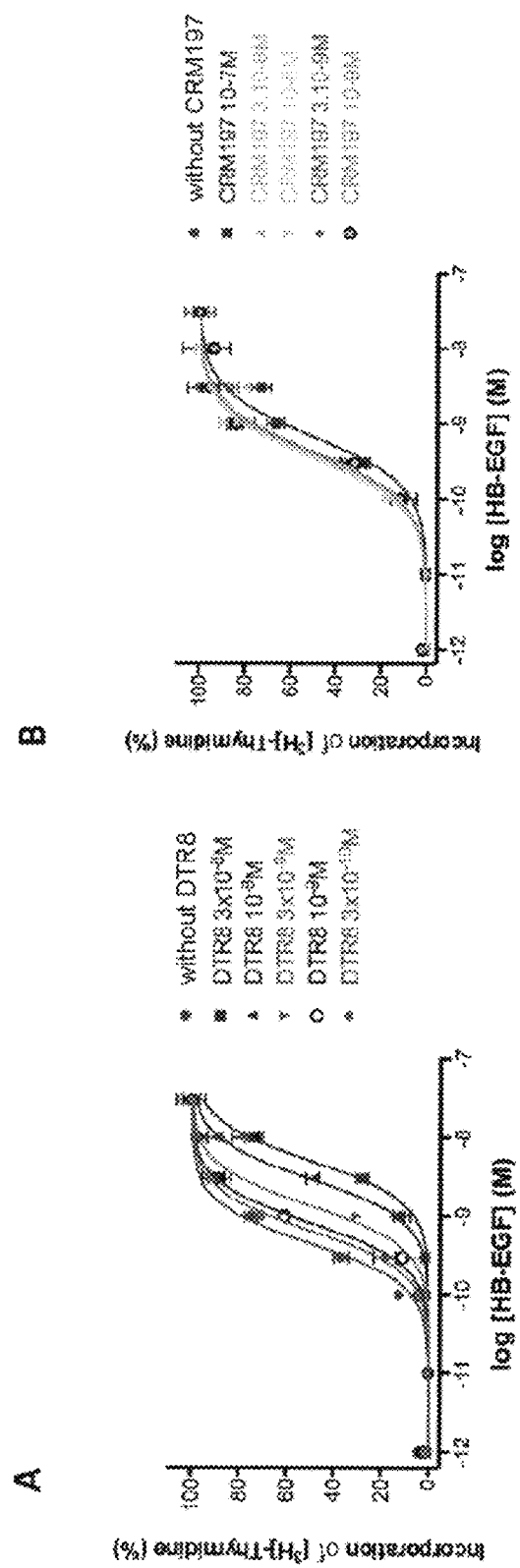
FIG. 6 represents the inhibition of the proliferative effect of increasing doses of HB-EGF on Ba/F3 cells expressing the EGFR and the growth of which is HB-EGF-dependent, by increasing doses of DTR8 (A) and of CRM197 (B)

The HB-EGF-binding activity of the DTR8 protein was also evaluated through its capacity to inhibit the binding of HB-EGF to the EGFR in a Ba/F3 cell line transfected with the EGFR gene and dependent on HB-EGF for its growth. The results (FIG. 6) show that DTR8 inhibits the proliferation of the HB-EGF-dependent cells in a dose-dependent manner. The inhibitory effect of DTR8 was compared with that of CRM197 (FIG. 6). The results show that at least 300 times more CRM197 is necessary in order to obtain an equivalent inhibitory effect. Consequently, DTR8 is at least 300 times more effective than CRM197 in terms of binding to HB-EGF in solution.

In conclusion, these results show that the DTR8 protein is capable of binding to pro-HB-EGF molecules at the surface of cells (FIG. 5) and to HB-EGF in solution (FIG. 6) and of blocking their biological activity. The estimation of the Kd values for the interactions suggests that DTR8 is 1400 times more powerful than CRM197 in terms of binding to HB-EGF.

EXAMPLE 5

Evaluation of the Antigenicity of the DTR1 and DTR8 Proteins

The western population is vaccinated against diphtheria toxin. Individuals who may benefit from treatment with a therapeutic protein of DTR8 type could therefore have antibodies capable of reacting against said protein. The capacity of the sera of 20 healthy donors to recognize diphtheria toxin (in its mutated form CRM197), and its various domains (catalytic (C), translocation (T) and DTR (in the soluble mutated form DTR1)) was compared with the DTR8 protein, by ELISA (FIG. 7). An antibody titer 20 corresponds to the background noise of the assay and therefore to an absence of recognition. A titer threshold at 30 was arbitrarily set in order to distinguish the sera exhibiting a weak or strong response.

The results (FIG. 7) show that 16/20 donors have antibodies against diphtheria toxin. 14/20 donors exhibit a medium to strong antibody response. However, the majority of the antibodies present in each serum considered individually are directed against the C domain of the toxin (FIG. 7). Indeed, 12 sera exhibit a response above the threshold (medium to strong response) and 4 sera exhibit a response below the threshold (weak response). If the reactivity of the sera against the soluble form of the R domain (DTR1) is considered, 15/20 sera recognize the R domain. However, only 7 sera exhibit a response above the threshold (medium to strong response). Notably, the DTR8 protein is considerably less well recognized by the sera of the donors than DTR1. Indeed, only 3/20 sera exhibit medium to strong reactivity against DTR8 and 2 sera exhibit weak reactivity (FIG. 7).

In conclusion, these results show that the antigenicity of the DTR8 protein is weak and considerably reduced compared with that of CRM197. This antigenicity is also reduced in comparison with that of the DTR1 protein, corresponding to the soluble form of DTR carrying the lowest number of mutations. In other words, the mutations introduced into DTR in order to increase its affinity for HB-EGF and to reduce its immunogenicity contribute to considerably reducing its antigenicity.

The invention claimed is:

1. A recombinant protein having at least 90% sequence identity with residues 380 to 535 of the amino acid sequence SEQ ID NO: 1, wherein the recombinant protein comprises at least the substitutions:

(i) Y380K or Y380E, and (ii) L390T, relative to SEQ ID NO: 1.

2. The protein of claim 1, comprising at least substitutions Y380K and L390T relative to SEQ ID NO: 1.

3. The protein of claim 2, further comprising at least a substitution Q387E relative to SEQ ID NO: 1.

4. The protein of claim 1, further comprising a substitution A395T relative to SEQ ID NO: 1.

5. The protein of claim 1, further comprising at least one substitution relative to SEQ ID NO: 1 selected from the group consisting of F389Y and G510A.

6. The protein of claim 1, further comprising at least one substitution relative to SEQ ID NO: 1 selected from the group consisting of: N399K, V452T, T517E, V483Q, H492E, S494K, T436H and E497D.

7. The protein of claim 1, comprising substitutions N399K, V452T, T517E, V483Q, H492E and S494K relative to SEQ ID NO: 1.

8. The protein of claim 1, comprising one of amino acid sequences SEQ ID NOs: 2 to 9.

9. The protein of claim 1, which is labeled with a detectable tracer.

10. The protein of claim 9, wherein the detectable tracer is a radioactive isotope or a fluorophore.

11. A pharmaceutical composition, comprising at least one recombinant protein of claim 1, and a pharmaceutically acceptable vehicle.

12. A method for treating a disease associated with activation of Heparin-Binding Epidermal Growth Factor (HB-EGF/EGFR) pathway in a subject in need thereof, the method comprising:

administering the recombinant protein of claim 1 to the subject, at a therapeutically effective amount, wherein the disease is selected from the group consisting of: rapidly progressive glomerulonephritis, ovarian cancer, endometrial cancer, breast cancer, uterine cancer, bladder cancer, stomach cancer, skin cancer, brain cancer, lung cancer, vasospasm associated with cerebral contusions, cardiac hypertrophy, smooth muscle cell hyperplasia, pulmonary hypertension, diabetic retinopathies and arterial restenosis.

13. A method for an in vitro diagnosis of a disease associated with activation of HB-EGF/EGFR pathway, the method comprising:

obtaining a biological sample from a subject, contacting the protein of claim 9 with the biological sample, thereby forming a complex between the protein and HB-EGF or pro-HB-EGF, detecting the presence of the complex, and diagnosing the subject as having the disease where the presence of the complex is detected, wherein the disease is selected from the group consisting of: rapidly progressive glomerulonephritis, ovarian cancer, endometrial cancer, breast cancer, uterine cancer, bladder cancer, stomach cancer, skin cancer, brain cancer, lung cancer, vasospasm associated with cerebral contusions, cardiac hypertrophy, smooth muscle cell hyperplasia, pulmonary hypertension, diabetic retinopathies and arterial restenosis.

14. The protein of claim 1, comprising at least substitutions Y380E and L390T relative to SEQ ID NO: 1.

* * * * *

```
                         SEQUENCE LISTING

<160> NUMBER OF SEQ ID NOS: 110

<210> SEQ ID NO 1
<211> LENGTH: 535
<212> TYPE: PRT
<213> ORGANISM: Corynebacterium diphtheriae

<400> SEQUENCE: 1

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335
```

```
Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
            355                 360                 365

Gln Val Val His Asn Ser Tyr Asn Arg Pro Ala Tyr Ser Pro Gly His
        370                 375                 380

Lys Thr Gln Pro Phe Leu His Asp Gly Tyr Ala Val Ser Trp Asn Thr
385                 390                 395                 400

Val Glu Asp Ser Ile Ile Arg Thr Gly Phe Gln Gly Glu Ser Gly His
                405                 410                 415

Asp Ile Lys Ile Thr Ala Glu Asn Thr Pro Leu Pro Ile Ala Gly Val
            420                 425                 430

Leu Leu Pro Thr Ile Pro Gly Lys Leu Asp Val Asn Lys Ser Lys Thr
            435                 440                 445

His Ile Ser Val Asn Gly Arg Lys Ile Arg Met Arg Cys Arg Ala Ile
        450                 455                 460

Asp Gly Asp Val Thr Phe Cys Arg Pro Lys Ser Pro Val Tyr Val Gly
465                 470                 475                 480

Asn Gly Val His Ala Asn Leu His Val Ala Phe His Arg Ser Ser Ser
                485                 490                 495

Glu Lys Ile His Ser Asn Glu Ile Ser Ser Asp Ser Ile Gly Val Leu
            500                 505                 510

Gly Tyr Gln Lys Thr Val Asp His Thr Lys Val Asn Ser Lys Leu Ser
        515                 520                 525

Leu Phe Phe Glu Ile Lys Ser
        530                 535

<210> SEQ ID NO 2
<211> LENGTH: 158
<212> TYPE: PRT
<213> ORGANISM: artificial sequence
<220> FEATURE:
<223> OTHER INFORMATION: synthetic protein (DTR variant Y380K/L390T
      encoded by clone 1D3)

<400> SEQUENCE: 2

Met Gly Lys Ser Pro Gly His Lys Thr Gln Pro Phe Thr His Asp Gly
1               5                   10                  15

Tyr Ala Val Ser Trp Asn Thr Val Glu Asp Ser Ile Ile Arg Thr Gly
            20                  25                  30

Phe Gln Gly Glu Ser Gly His Asp Ile Lys Ile Thr Ala Glu Asn Thr
        35                  40                  45

Pro Leu Pro Ile Ala Gly Val Leu Leu Pro Thr Ile Pro Gly Lys Leu
    50                  55                  60

Asp Val Asn Lys Ser Lys Thr His Ile Ser Val Asn Gly Arg Lys Ile
65                  70                  75                  80

Arg Met Arg Cys Arg Ala Ile Asp Gly Asp Val Thr Phe Cys Arg Pro
                85                  90                  95

Lys Ser Pro Val Tyr Val Gly Asn Gly Val His Ala Asn Leu His Val
            100                 105                 110

Ala Phe His Arg Ser Ser Ser Glu Lys Ile His Ser Asn Glu Ile Ser
        115                 120                 125

Ser Asp Ser Ile Gly Val Leu Gly Tyr Gln Lys Thr Val Asp His Thr
    130                 135                 140

Lys Val Asn Ser Lys Leu Ser Leu Phe Phe Glu Ile Lys Ser
```

<210> SEQ ID NO 3
<211> LENGTH: 158
<212> TYPE: PRT
<213> ORGANISM: artificial sequence
<220> FEATURE:
<223> OTHER INFORMATION: synthetic protein (DTR variant
      Y380K/Q387E/L390T encoded by clone 1D6)

<400> SEQUENCE: 3

Met Gly Lys Ser Pro Gly His Lys Thr Glu Pro Phe Thr His Asp Gly
1               5                   10                  15

Tyr Ala Val Ser Trp Asn Thr Val Glu Asp Ser Ile Ile Arg Thr Gly
            20                  25                  30

Phe Gln Gly Glu Ser Gly His Asp Ile Lys Ile Thr Ala Glu Asn Thr
        35                  40                  45

Pro Leu Pro Ile Ala Gly Val Leu Leu Pro Thr Ile Pro Gly Lys Leu
    50                  55                  60

Asp Val Asn Lys Ser Lys Thr His Ile Ser Val Asn Gly Arg Lys Ile
65                  70                  75                  80

Arg Met Arg Cys Arg Ala Ile Asp Gly Asp Val Thr Phe Cys Arg Pro
                85                  90                  95

Lys Ser Pro Val Tyr Val Gly Asn Gly Val His Ala Asn Leu His Val
            100                 105                 110

Ala Phe His Arg Ser Ser Glu Lys Ile His Ser Asn Glu Ile Ser
        115                 120                 125

Ser Asp Ser Ile Gly Val Leu Gly Tyr Gln Lys Thr Val Asp His Thr
    130                 135                 140

Lys Val Asn Ser Lys Leu Ser Leu Phe Phe Glu Ile Lys Ser
145                 150                 155

<210> SEQ ID NO 4
<211> LENGTH: 158
<212> TYPE: PRT
<213> ORGANISM: artificial sequence
<220> FEATURE:
<223> OTHER INFORMATION: synthetic protein (DTR variant
      Y380K/Q387E/P388T/L390T encoded by clone 2C8)

<400> SEQUENCE: 4

Met Gly Lys Ser Pro Gly His Lys Thr Glu Thr Phe Thr His Asp Gly
1               5                   10                  15

Tyr Ala Val Ser Trp Asn Thr Val Glu Asp Ser Ile Ile Arg Thr Gly
            20                  25                  30

Phe Gln Gly Glu Ser Gly His Asp Ile Lys Ile Thr Ala Glu Asn Thr
        35                  40                  45

Pro Leu Pro Ile Ala Gly Val Leu Leu Pro Thr Ile Pro Gly Lys Leu
    50                  55                  60

Asp Val Asn Lys Ser Lys Thr His Ile Ser Val Asn Gly Arg Lys Ile
65                  70                  75                  80

Arg Met Arg Cys Arg Ala Ile Asp Gly Asp Val Thr Phe Cys Arg Pro
                85                  90                  95

Lys Ser Pro Val Tyr Val Gly Asn Gly Val His Ala Asn Leu His Val
            100                 105                 110

Ala Phe His Arg Ser Ser Glu Lys Ile His Ser Asn Glu Ile Ser
        115                 120                 125

Ser Asp Ser Ile Gly Val Leu Gly Tyr Gln Lys Thr Val Asp His Thr

```
            130                 135                 140
Lys Val Asn Ser Lys Leu Ser Leu Phe Phe Glu Ile Lys Ser
145                 150                 155

<210> SEQ ID NO 5
<211> LENGTH: 158
<212> TYPE: PRT
<213> ORGANISM: artificial sequence
<220> FEATURE:
<223> OTHER INFORMATION: synthetic protein (DTR variant
      Y380K/P382T/Q387E/L390T encoded by clone 2G5)

<400> SEQUENCE: 5

Met Gly Lys Ser Thr Gly His Lys Thr Glu Pro Phe Thr His Asp Gly
1               5                   10                  15

Tyr Ala Val Ser Trp Asn Thr Val Glu Asp Ser Ile Ile Arg Thr Gly
                20                  25                  30

Phe Gln Gly Glu Ser Gly His Asp Ile Lys Ile Thr Ala Glu Asn Thr
            35                  40                  45

Pro Leu Pro Ile Ala Gly Val Leu Leu Pro Thr Ile Pro Gly Lys Leu
        50                  55                  60

Asp Val Asn Lys Ser Lys Thr His Ile Ser Val Asn Gly Arg Lys Ile
65                  70                  75                  80

Arg Met Arg Cys Arg Ala Ile Asp Gly Asp Val Thr Phe Cys Arg Pro
                85                  90                  95

Lys Ser Pro Val Tyr Val Gly Asn Gly Val His Ala Asn Leu His Val
                100                 105                 110

Ala Phe His Arg Ser Ser Ser Glu Lys Ile His Ser Asn Glu Ile Ser
            115                 120                 125

Ser Asp Ser Ile Gly Val Leu Gly Tyr Gln Lys Thr Val Asp His Thr
        130                 135                 140

Lys Val Asn Ser Lys Leu Ser Leu Phe Phe Glu Ile Lys Ser
145                 150                 155

<210> SEQ ID NO 6
<211> LENGTH: 158
<212> TYPE: PRT
<213> ORGANISM: artificial sequence
<220> FEATURE:
<223> OTHER INFORMATION: synthetic protein (DTR variant
      Y380E/P382T/Q387K/L390T encoded by clone 1H3)

<400> SEQUENCE: 6

Met Gly Glu Ser Thr Gly His Lys Thr Lys Pro Phe Thr His Asp Gly
1               5                   10                  15

Tyr Ala Val Ser Trp Asn Thr Val Glu Asp Ser Ile Ile Arg Thr Gly
                20                  25                  30

Phe Gln Gly Glu Ser Gly His Asp Ile Lys Ile Thr Ala Glu Asn Thr
            35                  40                  45

Pro Leu Pro Ile Ala Gly Val Leu Leu Pro Thr Ile Pro Gly Lys Leu
        50                  55                  60

Asp Val Asn Lys Ser Lys Thr His Ile Ser Val Asn Gly Arg Lys Ile
65                  70                  75                  80

Arg Met Arg Cys Arg Ala Ile Asp Gly Asp Val Thr Phe Cys Arg Pro
                85                  90                  95

Lys Ser Pro Val Tyr Val Gly Asn Gly Val His Ala Asn Leu His Val
                100                 105                 110

Ala Phe His Arg Ser Ser Ser Glu Lys Ile His Ser Asn Glu Ile Ser
```

```
              115                 120                 125
Ser Asp Ser Ile Gly Val Leu Gly Tyr Gln Lys Thr Val Asp His Thr
        130                 135                 140

Lys Val Asn Ser Lys Leu Ser Leu Phe Phe Glu Ile Lys Ser
145                 150                 155
```

<210> SEQ ID NO 7
<211> LENGTH: 158
<212> TYPE: PRT
<213> ORGANISM: artificial sequence
<220> FEATURE:
<223> OTHER INFORMATION: synthetic protein (DTR variant
      Y380K/Q387E/L390T/A395T named as DTR1)

<400> SEQUENCE: 7

```
Met Gly Lys Ser Pro Gly His Lys Thr Glu Pro Phe Thr His Asp Gly
1               5                   10                  15

Tyr Thr Val Ser Trp Asn Thr Val Glu Asp Ser Ile Ile Arg Thr Gly
                20                  25                  30

Phe Gln Gly Glu Ser Gly His Asp Ile Lys Ile Thr Ala Glu Asn Thr
            35                  40                  45

Pro Leu Pro Ile Ala Gly Val Leu Leu Pro Thr Ile Pro Gly Lys Leu
        50                  55                  60

Asp Val Asn Lys Ser Lys Thr His Ile Ser Val Asn Gly Arg Lys Ile
65                  70                  75                  80

Arg Met Arg Cys Arg Ala Ile Asp Gly Asp Val Thr Phe Cys Arg Pro
                85                  90                  95

Lys Ser Pro Val Tyr Val Gly Asn Gly Val His Ala Asn Leu His Val
            100                 105                 110

Ala Phe His Arg Ser Ser Ser Glu Lys Ile His Ser Asn Glu Ile Ser
        115                 120                 125

Ser Asp Ser Ile Gly Val Leu Gly Tyr Gln Lys Thr Val Asp His Thr
    130                 135                 140

Lys Val Asn Ser Lys Leu Ser Leu Phe Phe Glu Ile Lys Ser
145                 150                 155
```

<210> SEQ ID NO 8
<211> LENGTH: 158
<212> TYPE: PRT
<213> ORGANISM: artificial sequence
<220> FEATURE:
<223> OTHER INFORMATION: synthetic protein (DTR variant
      Y380K/Q387E/F389Y/L390T/A395T/G510A named as DTR3)

<400> SEQUENCE: 8

```
Met Gly Lys Ser Pro Gly His Lys Thr Glu Pro Tyr Thr His Asp Gly
1               5                   10                  15

Tyr Thr Val Ser Trp Asn Thr Val Glu Asp Ser Ile Ile Arg Thr Gly
                20                  25                  30

Phe Gln Gly Glu Ser Gly His Asp Ile Lys Ile Thr Ala Glu Asn Thr
            35                  40                  45

Pro Leu Pro Ile Ala Gly Val Leu Leu Pro Thr Ile Pro Gly Lys Leu
        50                  55                  60

Asp Val Asn Lys Ser Lys Thr His Ile Ser Val Asn Gly Arg Lys Ile
65                  70                  75                  80

Arg Met Arg Cys Arg Ala Ile Asp Gly Asp Val Thr Phe Cys Arg Pro
                85                  90                  95

Lys Ser Pro Val Tyr Val Gly Asn Gly Val His Ala Asn Leu His Val
```

```
                    100                 105                 110
Ala Phe His Arg Ser Ser Glu Lys Ile His Ser Asn Glu Ile Ser
            115                 120                 125

Ser Asp Ser Ile Ala Val Leu Gly Tyr Gln Lys Thr Val Asp His Thr
        130                 135                 140

Lys Val Asn Ser Lys Leu Ser Leu Phe Phe Glu Ile Lys Ser
145                 150                 155
```

<210> SEQ ID NO 9
<211> LENGTH: 158
<212> TYPE: PRT
<213> ORGANISM: artificial sequence
<220> FEATURE:
<223> OTHER INFORMATION: synthetic protein (DTRvariant
    Y380K/Q387E/F389Y/L390T/A395T/N399K/V452T/V483Q/H492E/S494K/
    G510A/T517E named as DTR8)

<400> SEQUENCE: 9

```
Met Gly Lys Ser Pro Gly His Lys Thr Glu Pro Tyr Thr His Asp Gly
1               5                   10                  15

Tyr Thr Val Ser Trp Lys Thr Val Glu Asp Ser Ile Ile Arg Thr Gly
            20                  25                  30

Phe Gln Gly Glu Ser Gly His Asp Ile Lys Ile Thr Ala Glu Asn Thr
        35                  40                  45

Pro Leu Pro Ile Ala Gly Val Leu Leu Pro Thr Ile Pro Gly Lys Leu
    50                  55                  60

Asp Val Asn Lys Ser Lys Thr His Ile Ser Thr Asn Gly Arg Lys Ile
65                  70                  75                  80

Arg Met Arg Cys Arg Ala Ile Asp Gly Asp Val Thr Phe Cys Arg Pro
                85                  90                  95

Lys Ser Pro Val Tyr Val Gly Asn Gly Gln His Ala Asn Leu His Val
            100                 105                 110

Ala Phe Glu Arg Lys Ser Ser Glu Lys Ile His Ser Asn Glu Ile Ser
        115                 120                 125

Ser Asp Ser Ile Ala Val Leu Gly Tyr Gln Lys Glu Val Asp His Thr
    130                 135                 140

Lys Val Asn Ser Lys Leu Ser Leu Phe Phe Glu Ile Lys Ser
145                 150                 155
```

<210> SEQ ID NO 10
<211> LENGTH: 477
<212> TYPE: DNA
<213> ORGANISM: artificial sequence
<220> FEATURE:
<223> OTHER INFORMATION: synthetic polynucleotide (optimized coding
    sequence for DTR1)
<220> FEATURE:
<221> NAME/KEY: CDS
<222> LOCATION: (1)..(474)

<400> SEQUENCE: 10

```
atg ggc aaa agc ccg ggt cat aaa acc gag ccg ttt acc cat gat ggc      48
Met Gly Lys Ser Pro Gly His Lys Thr Glu Pro Phe Thr His Asp Gly
1               5                   10                  15 tat acc gtg agc tgg aac acc gtg gaa gat agc att att cgt acc ggc      96
Tyr Thr Val Ser Trp Asn Thr Val Glu Asp Ser Ile Ile Arg Thr Gly
            20                  25                  30 ttt cag ggc gaa agc ggc cat gat att aaa att acc gcg gaa aac acc     144
Phe Gln Gly Glu Ser Gly His Asp Ile Lys Ile Thr Ala Glu Asn Thr
        35                  40                  45
```

```
ccg ctg ccg att gcg ggt gtt ctg ctg ccg acc att ccg ggc aaa ctg    192
Pro Leu Pro Ile Ala Gly Val Leu Leu Pro Thr Ile Pro Gly Lys Leu
 50                  55                  60 gat gtg aac aaa agc aaa acc cat att agc gtg aac ggc cgt aaa att    240
Asp Val Asn Lys Ser Lys Thr His Ile Ser Val Asn Gly Arg Lys Ile
 65                  70                  75                  80 cgt atg cgt tgc cgt gcg att gat ggt gat gtg acc ttt tgc cgt ccg    288
Arg Met Arg Cys Arg Ala Ile Asp Gly Asp Val Thr Phe Cys Arg Pro
                 85                  90                  95 aaa agc ccg gtg tat gtg ggc aac ggc gtg cat gcg aac ctg cat gtg    336
Lys Ser Pro Val Tyr Val Gly Asn Gly Val His Ala Asn Leu His Val
            100                 105                 110 gcg ttt cat cgt agc agc agc gaa aaa atc cat agc aac gaa att agc    384
Ala Phe His Arg Ser Ser Ser Glu Lys Ile His Ser Asn Glu Ile Ser
        115                 120                 125 agc gat agc att ggc gtg ctg ggc tat cag aaa acc gtg gat cat acc    432
Ser Asp Ser Ile Gly Val Leu Gly Tyr Gln Lys Thr Val Asp His Thr
    130                 135                 140 aaa gtg aac tct aaa ctg agc ctg ttc ttc gaa atc aaa agc tga        477
Lys Val Asn Ser Lys Leu Ser Leu Phe Phe Glu Ile Lys Ser
145                 150                 155
```

<210> SEQ ID NO 11
<211> LENGTH: 158
<212> TYPE: PRT
<213> ORGANISM: artificial sequence
<220> FEATURE:
<223> OTHER INFORMATION: Synthetic Construct

<400> SEQUENCE: 11

```
Met Gly Lys Ser Pro Gly His Lys Thr Glu Pro Phe Thr His Asp Gly
 1               5                  10                  15

Tyr Thr Val Ser Trp Asn Thr Val Glu Asp Ser Ile Ile Arg Thr Gly
             20                  25                  30

Phe Gln Gly Glu Ser Gly His Asp Ile Lys Ile Thr Ala Glu Asn Thr
         35                  40                  45

Pro Leu Pro Ile Ala Gly Val Leu Leu Pro Thr Ile Pro Gly Lys Leu
 50                  55                  60

Asp Val Asn Lys Ser Lys Thr His Ile Ser Val Asn Gly Arg Lys Ile
 65                  70                  75                  80

Arg Met Arg Cys Arg Ala Ile Asp Gly Asp Val Thr Phe Cys Arg Pro
                 85                  90                  95

Lys Ser Pro Val Tyr Val Gly Asn Gly Val His Ala Asn Leu His Val
            100                 105                 110

Ala Phe His Arg Ser Ser Ser Glu Lys Ile His Ser Asn Glu Ile Ser
        115                 120                 125

Ser Asp Ser Ile Gly Val Leu Gly Tyr Gln Lys Thr Val Asp His Thr
    130                 135                 140

Lys Val Asn Ser Lys Leu Ser Leu Phe Phe Glu Ile Lys Ser
145                 150                 155
```

<210> SEQ ID NO 12
<211> LENGTH: 477
<212> TYPE: DNA
<213> ORGANISM: artificial sequence
<220> FEATURE:
<223> OTHER INFORMATION: synthetic polynucleotide (optimized coding
      sequence for DTR3)
<220> FEATURE:
<221> NAME/KEY: CDS
<222> LOCATION: (1)..(474)

<400> SEQUENCE: 12

```
atg ggc aaa agc ccg ggt cat aaa acc gag ccg tat acc cat gat ggc      48
Met Gly Lys Ser Pro Gly His Lys Thr Glu Pro Tyr Thr His Asp Gly
1               5                   10                  15 tat acc gtg agc tgg aac acc gtg gaa gat agc att att cgt acc ggc      96
Tyr Thr Val Ser Trp Asn Thr Val Glu Asp Ser Ile Ile Arg Thr Gly
            20                  25                  30 ttt cag ggc gaa agc ggc cat gat att aaa att acc gcg gaa aac acc     144
Phe Gln Gly Glu Ser Gly His Asp Ile Lys Ile Thr Ala Glu Asn Thr
        35                  40                  45 ccg ctg ccg att gcg ggt gtt ctg ctg ccg acc att ccg ggc aaa ctg     192
Pro Leu Pro Ile Ala Gly Val Leu Leu Pro Thr Ile Pro Gly Lys Leu
    50                  55                  60 gat gtg aac aaa agc aaa acc cat att agc gtg aac ggc cgt aaa att     240
Asp Val Asn Lys Ser Lys Thr His Ile Ser Val Asn Gly Arg Lys Ile
65                  70                  75                  80 cgt atg cgt tgc cgt gcg att gat ggt gat gtg acc ttt tgc cgt ccg     288
Arg Met Arg Cys Arg Ala Ile Asp Gly Asp Val Thr Phe Cys Arg Pro
                85                  90                  95 aaa agc ccg gtg tat gtg ggc aac ggc gtg cat gcg aac ctg cat gtg     336
Lys Ser Pro Val Tyr Val Gly Asn Gly Val His Ala Asn Leu His Val
            100                 105                 110 gcg ttt cat cgt agc agc agc gaa aaa atc cat agc aac gaa att agc     384
Ala Phe His Arg Ser Ser Ser Glu Lys Ile His Ser Asn Glu Ile Ser
        115                 120                 125 agc gat agc att gcg gtg ctg ggc tat cag aaa acc gtg gat cat acc     432
Ser Asp Ser Ile Ala Val Leu Gly Tyr Gln Lys Thr Val Asp His Thr
    130                 135                 140 aaa gtg aac tct aaa ctg agc ctg ttc ttc gaa atc aaa agc tga         477
Lys Val Asn Ser Lys Leu Ser Leu Phe Phe Glu Ile Lys Ser
145                 150                 155
```

<210> SEQ ID NO 13
<211> LENGTH: 158
<212> TYPE: PRT
<213> ORGANISM: artificial sequence
<220> FEATURE:
<223> OTHER INFORMATION: Synthetic Construct

<400> SEQUENCE: 13

```
Met Gly Lys Ser Pro Gly His Lys Thr Glu Pro Tyr Thr His Asp Gly
1               5                   10                  15

Tyr Thr Val Ser Trp Asn Thr Val Glu Asp Ser Ile Ile Arg Thr Gly
            20                  25                  30

Phe Gln Gly Glu Ser Gly His Asp Ile Lys Ile Thr Ala Glu Asn Thr
        35                  40                  45

Pro Leu Pro Ile Ala Gly Val Leu Leu Pro Thr Ile Pro Gly Lys Leu
    50                  55                  60

Asp Val Asn Lys Ser Lys Thr His Ile Ser Val Asn Gly Arg Lys Ile
65                  70                  75                  80

Arg Met Arg Cys Arg Ala Ile Asp Gly Asp Val Thr Phe Cys Arg Pro
                85                  90                  95

Lys Ser Pro Val Tyr Val Gly Asn Gly Val His Ala Asn Leu His Val
            100                 105                 110

Ala Phe His Arg Ser Ser Ser Glu Lys Ile His Ser Asn Glu Ile Ser
        115                 120                 125

Ser Asp Ser Ile Ala Val Leu Gly Tyr Gln Lys Thr Val Asp His Thr
    130                 135                 140
```

Lys Val Asn Ser Lys Leu Ser Leu Phe Phe Glu Ile Lys Ser
145                 150                 155

<210> SEQ ID NO 14
<211> LENGTH: 477
<212> TYPE: DNA
<213> ORGANISM: artificial sequence
<220> FEATURE:
<223> OTHER INFORMATION: synthetic polynucleotide (optimized coding
      sequence for DTR8)
<220> FEATURE:
<221> NAME/KEY: CDS
<222> LOCATION: (1)..(474)

<400> SEQUENCE: 14

```
atg ggc aaa agc ccg ggt cat aaa acc gag ccg tat acc cat gat ggc     48
Met Gly Lys Ser Pro Gly His Lys Thr Glu Pro Tyr Thr His Asp Gly
1               5                   10                  15 tat acc gtg agc tgg aaa acc gtg gaa gat agc att att cgt acc ggc     96
Tyr Thr Val Ser Trp Lys Thr Val Glu Asp Ser Ile Ile Arg Thr Gly
            20                  25                  30 ttt cag ggc gaa agc ggc cat gat att aaa att acc gcg gaa aac acc    144
Phe Gln Gly Glu Ser Gly His Asp Ile Lys Ile Thr Ala Glu Asn Thr
        35                  40                  45 ccg ctg ccg att gcg ggt gtt ctg ctg ccg acc att ccg ggc aaa ctg    192
Pro Leu Pro Ile Ala Gly Val Leu Leu Pro Thr Ile Pro Gly Lys Leu
    50                  55                  60 gat gtg aac aaa agc aaa acc cat att agc acg aac ggc cgt aaa att    240
Asp Val Asn Lys Ser Lys Thr His Ile Ser Thr Asn Gly Arg Lys Ile
65                  70                  75                  80 cgt atg cgt tgc cgt gcg att gat ggt gat gtg acc ttt tgc cgt ccg    288
Arg Met Arg Cys Arg Ala Ile Asp Gly Asp Val Thr Phe Cys Arg Pro
                85                  90                  95 aaa agc ccg gtg tat gtg ggc aac ggc cag cat gcg aac ctg cat gtg    336
Lys Ser Pro Val Tyr Val Gly Asn Gly Gln His Ala Asn Leu His Val
            100                 105                 110 gcg ttt gaa cgt aaa agc agc gaa aaa atc cat agc aac gaa att agc    384
Ala Phe Glu Arg Lys Ser Ser Glu Lys Ile His Ser Asn Glu Ile Ser
        115                 120                 125 agc gat agc att gcg gtg ctg ggc tat cag aaa gaa gtg gat cat acc    432
Ser Asp Ser Ile Ala Val Leu Gly Tyr Gln Lys Glu Val Asp His Thr
    130                 135                 140 aaa gtg aac tct aaa ctg agc ctg ttc ttc gaa atc aaa agc tga        477
Lys Val Asn Ser Lys Leu Ser Leu Phe Phe Glu Ile Lys Ser
145                 150                 155
```

<210> SEQ ID NO 15
<211> LENGTH: 158
<212> TYPE: PRT
<213> ORGANISM: artificial sequence
<220> FEATURE:
<223> OTHER INFORMATION: Synthetic Construct

<400> SEQUENCE: 15

Met Gly Lys Ser Pro Gly His Lys Thr Glu Pro Tyr Thr His Asp Gly
1               5                   10                  15

Tyr Thr Val Ser Trp Lys Thr Val Glu Asp Ser Ile Ile Arg Thr Gly
            20                  25                  30

Phe Gln Gly Glu Ser Gly His Asp Ile Lys Ile Thr Ala Glu Asn Thr
        35                  40                  45

Pro Leu Pro Ile Ala Gly Val Leu Leu Pro Thr Ile Pro Gly Lys Leu
    50                  55                  60

```
Asp Val Asn Lys Ser Lys Thr His Ile Ser Thr Asn Gly Arg Lys Ile
 65                  70                  75                  80

Arg Met Arg Cys Arg Ala Ile Asp Gly Asp Val Thr Phe Cys Arg Pro
                 85                  90                  95

Lys Ser Pro Val Tyr Val Gly Asn Gly Gln His Ala Asn Leu His Val
            100                 105                 110

Ala Phe Glu Arg Lys Ser Ser Glu Lys Ile His Ser Asn Glu Ile Ser
        115                 120                 125

Ser Asp Ser Ile Ala Val Leu Gly Tyr Gln Lys Glu Val Asp His Thr
    130                 135                 140

Lys Val Asn Ser Lys Leu Ser Leu Phe Phe Glu Ile Lys Ser
145                 150                 155
```

<210> SEQ ID NO 16
<211> LENGTH: 477
<212> TYPE: DNA
<213> ORGANISM: artificial sequence
<220> FEATURE:
<223> OTHER INFORMATION: synthetic polynucleotide (optimized coding sequence for DTRwt)
<220> FEATURE:
<221> NAME/KEY: CDS
<222> LOCATION: (1)..(474)

<400> SEQUENCE: 16

```
atg ggc tac agc ccg ggt cat aaa acc cag ccg ttt ctg cat gat ggc      48
Met Gly Tyr Ser Pro Gly His Lys Thr Gln Pro Phe Leu His Asp Gly
 1               5                  10                  15 tat gcg gtg agc tgg aac acc gtg gaa gat agc att att cgt acc ggc      96
Tyr Ala Val Ser Trp Asn Thr Val Glu Asp Ser Ile Ile Arg Thr Gly
                20                  25                  30 ttt cag ggc gaa agc ggc cat gat att aaa att acc gcg gaa aac acc    144
Phe Gln Gly Glu Ser Gly His Asp Ile Lys Ile Thr Ala Glu Asn Thr
            35                  40                  45 ccg ctg ccg att gcg ggt gtt ctg ctg ccg acc att ccg ggc aaa ctg    192
Pro Leu Pro Ile Ala Gly Val Leu Leu Pro Thr Ile Pro Gly Lys Leu
    50                  55                  60 gat gtg aac aaa agc aaa acc cat att agc gtg aac ggc cgt aaa att    240
Asp Val Asn Lys Ser Lys Thr His Ile Ser Val Asn Gly Arg Lys Ile
65                  70                  75                  80 cgt atg cgt tgc cgt gcg att gat ggt gat gtg acc ttt tgc cgt ccg    288
Arg Met Arg Cys Arg Ala Ile Asp Gly Asp Val Thr Phe Cys Arg Pro
                85                  90                  95 aaa agc ccg gtg tat gtg ggc aac ggc gtg cat gcg aac ctg cat gtg    336
Lys Ser Pro Val Tyr Val Gly Asn Gly Val His Ala Asn Leu His Val
            100                 105                 110 gcg ttt cat cgt agc agc agc gaa aaa atc cat agc aac gaa att agc    384
Ala Phe His Arg Ser Ser Ser Glu Lys Ile His Ser Asn Glu Ile Ser
        115                 120                 125 agc gat agc att ggc gtg ctg ggc tat cag aaa acc gtg gat cat acc    432
Ser Asp Ser Ile Gly Val Leu Gly Tyr Gln Lys Thr Val Asp His Thr
    130                 135                 140 aaa gtg aac tct aaa ctg agc ctg ttc ttc gaa atc aaa agc tga        477
Lys Val Asn Ser Lys Leu Ser Leu Phe Phe Glu Ile Lys Ser
145                 150                 155
```

<210> SEQ ID NO 17
<211> LENGTH: 158
<212> TYPE: PRT
<213> ORGANISM: artificial sequence
<220> FEATURE:

<223> OTHER INFORMATION: Synthetic Construct

<400> SEQUENCE: 17

```
Met Gly Tyr Ser Pro Gly His Lys Thr Gln Pro Phe Leu His Asp Gly
1               5                   10                  15

Tyr Ala Val Ser Trp Asn Thr Val Glu Asp Ser Ile Ile Arg Thr Gly
            20                  25                  30

Phe Gln Gly Glu Ser Gly His Asp Ile Lys Ile Thr Ala Glu Asn Thr
        35                  40                  45

Pro Leu Pro Ile Ala Gly Val Leu Leu Pro Thr Ile Pro Gly Lys Leu
    50                  55                  60

Asp Val Asn Lys Ser Lys Thr His Ile Ser Val Asn Gly Arg Lys Ile
65                  70                  75                  80

Arg Met Arg Cys Arg Ala Ile Asp Gly Asp Val Thr Phe Cys Arg Pro
                85                  90                  95

Lys Ser Pro Val Tyr Val Gly Asn Gly Val His Ala Asn Leu His Val
            100                 105                 110

Ala Phe His Arg Ser Ser Ser Glu Lys Ile His Ser Asn Glu Ile Ser
        115                 120                 125

Ser Asp Ser Ile Gly Val Leu Gly Tyr Gln Lys Thr Val Asp His Thr
    130                 135                 140

Lys Val Asn Ser Lys Leu Ser Leu Phe Phe Glu Ile Lys Ser
145                 150                 155
```

<210> SEQ ID NO 18
<211> LENGTH: 15
<212> TYPE: PRT
<213> ORGANISM: artificial sequence
<220> FEATURE:
<223> OTHER INFORMATION: synthetic peptide (peptide 1: DTR 378-392)

<400> SEQUENCE: 18

```
Met Gly Tyr Ser Pro Gly His Lys Thr Gln Pro Phe Leu His Asp
1               5                   10                  15
```

<210> SEQ ID NO 19
<211> LENGTH: 15
<212> TYPE: PRT
<213> ORGANISM: artificial sequence
<220> FEATURE:
<223> OTHER INFORMATION: synthetic peptide (peptide 2: DTR 385-399)

<400> SEQUENCE: 19

```
Lys Thr Gln Pro Phe Leu His Asp Gly Tyr Ala Val Ser Trp Asn
1               5                   10                  15
```

<210> SEQ ID NO 20
<211> LENGTH: 15
<212> TYPE: PRT
<213> ORGANISM: artificial sequence
<220> FEATURE:
<223> OTHER INFORMATION: synthetic peptide (peptide 3: DTR 391-405)

<400> SEQUENCE: 20

```
His Asp Gly Tyr Ala Val Ser Trp Asn Thr Val Glu Asp Ser Ile
1               5                   10                  15
```

<210> SEQ ID NO 21
<211> LENGTH: 15
<212> TYPE: PRT
<213> ORGANISM: artificial sequence
<220> FEATURE:

<223> OTHER INFORMATION: synthetic peptide (peptide 4: DTR 397-411)

<400> SEQUENCE: 21

Ser Trp Asn Thr Val Glu Asp Ser Ile Ile Arg Thr Gly Phe Gln
1               5                   10                  15

<210> SEQ ID NO 22
<211> LENGTH: 15
<212> TYPE: PRT
<213> ORGANISM: artificial sequence
<220> FEATURE:
<223> OTHER INFORMATION: synthetic peptide (peptide 5: DTR 403-417)

<400> SEQUENCE: 22

Asp Ser Ile Ile Arg Thr Gly Phe Gln Gly Glu Ser Gly His Asp
1               5                   10                  15

<210> SEQ ID NO 23
<211> LENGTH: 15
<212> TYPE: PRT
<213> ORGANISM: artificial sequence
<220> FEATURE:
<223> OTHER INFORMATION: synthetic peptide (peptide 6: DTR 409-423)

<400> SEQUENCE: 23

Gly Phe Gln Gly Glu Ser Gly His Asp Ile Lys Ile Thr Ala Glu
1               5                   10                  15

<210> SEQ ID NO 24
<211> LENGTH: 15
<212> TYPE: PRT
<213> ORGANISM: artificial sequence
<220> FEATURE:
<223> OTHER INFORMATION: synthetic peptide (peptide 7: DTR 415-429)

<400> SEQUENCE: 24

Gly His Asp Ile Lys Ile Thr Ala Glu Asn Thr Pro Leu Pro Ile
1               5                   10                  15

<210> SEQ ID NO 25
<211> LENGTH: 15
<212> TYPE: PRT
<213> ORGANISM: artificial sequence
<220> FEATURE:
<223> OTHER INFORMATION: synthetic peptide (peptide 8: DTR 421-435)

<400> SEQUENCE: 25

Thr Ala Glu Asn Thr Pro Leu Pro Ile Ala Gly Val Leu Leu Pro
1               5                   10                  15

<210> SEQ ID NO 26
<211> LENGTH: 15
<212> TYPE: PRT
<213> ORGANISM: artificial sequence
<220> FEATURE:
<223> OTHER INFORMATION: synthetic peptide (peptide 9: DTR 427-441)

<400> SEQUENCE: 26

Leu Pro Ile Ala Gly Val Leu Leu Pro Thr Ile Pro Gly Lys Leu
1               5                   10                  15

<210> SEQ ID NO 27
<211> LENGTH: 15
<212> TYPE: PRT
<213> ORGANISM: artificial sequence
<220> FEATURE:
<223> OTHER INFORMATION: synthetic peptide (peptide 10: DTR 433-447)

```
<400> SEQUENCE: 27

Leu Leu Pro Thr Ile Pro Gly Lys Leu Asp Val Asn Lys Ser Lys
1               5                   10                  15

<210> SEQ ID NO 28
<211> LENGTH: 15
<212> TYPE: PRT
<213> ORGANISM: artificial sequence
<220> FEATURE:
<223> OTHER INFORMATION: synthetic peptide (peptide 11: DTR 439-453)

<400> SEQUENCE: 28

Gly Lys Leu Asp Val Asn Lys Ser Lys Thr His Ile Ser Val Asn
1               5                   10                  15

<210> SEQ ID NO 29
<211> LENGTH: 15
<212> TYPE: PRT
<213> ORGANISM: artificial sequence
<220> FEATURE:
<223> OTHER INFORMATION: synthetic peptide (peptide 12: DTR 445-459)

<400> SEQUENCE: 29

Lys Ser Lys Thr His Ile Ser Val Asn Gly Arg Lys Ile Arg Met
1               5                   10                  15

<210> SEQ ID NO 30
<211> LENGTH: 15
<212> TYPE: PRT
<213> ORGANISM: artificial sequence
<220> FEATURE:
<223> OTHER INFORMATION: synthetic peptide (peptide 13: DTR 451-465)

<400> SEQUENCE: 30

Ser Val Asn Gly Arg Lys Ile Arg Met Arg Cys Arg Ala Ile Asp
1               5                   10                  15

<210> SEQ ID NO 31
<211> LENGTH: 15
<212> TYPE: PRT
<213> ORGANISM: artificial sequence
<220> FEATURE:
<223> OTHER INFORMATION: synthetic peptide (peptide 14: DTR 457-471)

<400> SEQUENCE: 31

Ile Arg Met Arg Cys Arg Ala Ile Asp Gly Asp Val Thr Phe Cys
1               5                   10                  15

<210> SEQ ID NO 32
<211> LENGTH: 15
<212> TYPE: PRT
<213> ORGANISM: artificial sequence
<220> FEATURE:
<223> OTHER INFORMATION: synthetic peptide (peptide 15: DTR 463-477)

<400> SEQUENCE: 32

Ala Ile Asp Gly Asp Val Thr Phe Cys Arg Pro Lys Ser Pro Val
1               5                   10                  15

<210> SEQ ID NO 33
<211> LENGTH: 15
<212> TYPE: PRT
<213> ORGANISM: artificial sequence
<220> FEATURE:
<223> OTHER INFORMATION: synthetic peptide (peptide 16: DTR 469-483)
```

<400> SEQUENCE: 33

Thr Phe Cys Arg Pro Lys Ser Pro Val Tyr Val Gly Asn Gly Val
1               5                   10                  15

<210> SEQ ID NO 34
<211> LENGTH: 15
<212> TYPE: PRT
<213> ORGANISM: artificial sequence
<220> FEATURE:
<223> OTHER INFORMATION: synthetic peptide (peptide 17: DTR 475-489)

<400> SEQUENCE: 34

Ser Pro Val Tyr Val Gly Asn Gly Val His Ala Asn Leu His Val
1               5                   10                  15

<210> SEQ ID NO 35
<211> LENGTH: 15
<212> TYPE: PRT
<213> ORGANISM: artificial sequence
<220> FEATURE:
<223> OTHER INFORMATION: synthetic peptide (peptide 18: DTR 482-496)

<400> SEQUENCE: 35

Gly Val His Ala Asn Leu His Val Ala Phe His Arg Ser Ser Ser
1               5                   10                  15

<210> SEQ ID NO 36
<211> LENGTH: 15
<212> TYPE: PRT
<213> ORGANISM: artificial sequence
<220> FEATURE:
<223> OTHER INFORMATION: synthetic peptide (peptide 19: DTR 488-502)

<400> SEQUENCE: 36

His Val Ala Phe His Arg Ser Ser Ser Glu Lys Ile His Ser Asn
1               5                   10                  15

<210> SEQ ID NO 37
<211> LENGTH: 15
<212> TYPE: PRT
<213> ORGANISM: artificial sequence
<220> FEATURE:
<223> OTHER INFORMATION: synthetic peptide (peptide 20: DTR 494-508)

<400> SEQUENCE: 37

Ser Ser Ser Glu Lys Ile His Ser Asn Glu Ile Ser Ser Asp Ser
1               5                   10                  15

<210> SEQ ID NO 38
<211> LENGTH: 15
<212> TYPE: PRT
<213> ORGANISM: artificial sequence
<220> FEATURE:
<223> OTHER INFORMATION: synthetic peptide (peptide 21: DTR 500-514)

<400> SEQUENCE: 38

His Ser Asn Glu Ile Ser Ser Asp Ser Ile Gly Val Leu Gly Tyr
1               5                   10                  15

<210> SEQ ID NO 39
<211> LENGTH: 15
<212> TYPE: PRT
<213> ORGANISM: artificial sequence
<220> FEATURE:
<223> OTHER INFORMATION: synthetic peptide (peptide 22: DTR 506-520)

<400> SEQUENCE: 39

Ser Asp Ser Ile Gly Val Leu Gly Tyr Gln Lys Thr Val Asp His
1               5                   10                  15

<210> SEQ ID NO 40
<211> LENGTH: 15
<212> TYPE: PRT
<213> ORGANISM: artificial sequence
<220> FEATURE:
<223> OTHER INFORMATION: synthetic peptide (peptide 23: DTR 512-526)

<400> SEQUENCE: 40

Leu Gly Tyr Gln Lys Thr Val Asp His Thr Lys Val Asn Ser Lys
1               5                   10                  15

<210> SEQ ID NO 41
<211> LENGTH: 15
<212> TYPE: PRT
<213> ORGANISM: artificial sequence
<220> FEATURE:
<223> OTHER INFORMATION: synthetic peptide (peptide 24: DTR 518-532)

<400> SEQUENCE: 41

Val Asp His Thr Lys Val Asn Ser Lys Leu Ser Leu Phe Phe Glu
1               5                   10                  15

<210> SEQ ID NO 42
<211> LENGTH: 15
<212> TYPE: PRT
<213> ORGANISM: artificial sequence
<220> FEATURE:
<223> OTHER INFORMATION: synthetic peptide (peptide 25: DTR 521-535)

<400> SEQUENCE: 42

Thr Lys Val Asn Ser Lys Leu Ser Leu Phe Phe Glu Ile Lys Ser
1               5                   10                  15

<210> SEQ ID NO 43
<211> LENGTH: 26
<212> TYPE: PRT
<213> ORGANISM: artificial sequence
<220> FEATURE:
<223> OTHER INFORMATION: synthetic peptide (DTRwt 378-403)

<400> SEQUENCE: 43

Met Gly Tyr Ser Pro Gly His Lys Thr Gln Pro Phe Leu His Asp Gly
1               5                   10                  15

Tyr Ala Val Ser Trp Asn Thr Val Glu Asp
            20                  25

<210> SEQ ID NO 44
<211> LENGTH: 26
<212> TYPE: PRT
<213> ORGANISM: artificial sequence
<220> FEATURE:
<223> OTHER INFORMATION: synthetic peptide (DTR1 378-403)

<400> SEQUENCE: 44

Met Gly Lys Ser Pro Gly His Lys Thr Glu Pro Phe Thr His Asp Gly
1               5                   10                  15

Tyr Thr Val Ser Trp Asn Thr Val Glu Asp
            20                  25

<210> SEQ ID NO 45
<211> LENGTH: 9
<212> TYPE: PRT

```
<213> ORGANISM: artificial sequence
<220> FEATURE:
<223> OTHER INFORMATION: synthetic peptide (DTRwt 389-397)

<400> SEQUENCE: 45

Phe Leu His Asp Gly Tyr Ala Val Ser
1               5

<210> SEQ ID NO 46
<211> LENGTH: 9
<212> TYPE: PRT
<213> ORGANISM: artificial sequence
<220> FEATURE:
<223> OTHER INFORMATION: synthetic peptide (DTRwt 394-402)

<400> SEQUENCE: 46

Tyr Ala Val Ser Trp Asn Thr Val Glu
1               5

<210> SEQ ID NO 47
<211> LENGTH: 9
<212> TYPE: PRT
<213> ORGANISM: artificial sequence
<220> FEATURE:
<223> OTHER INFORMATION: synthetic peptide (DTR1 389-397)

<400> SEQUENCE: 47

Phe Thr His Asp Gly Tyr Thr Val Ser
1               5

<210> SEQ ID NO 48
<211> LENGTH: 9
<212> TYPE: PRT
<213> ORGANISM: artificial sequence
<220> FEATURE:
<223> OTHER INFORMATION: synthetic peptide (DTR1 394-402)

<400> SEQUENCE: 48

Tyr Thr Val Ser Trp Asn Thr Val Glu
1               5

<210> SEQ ID NO 49
<211> LENGTH: 21
<212> TYPE: PRT
<213> ORGANISM: artificial sequence
<220> FEATURE:
<223> OTHER INFORMATION: synthetic peptide (DTR1 391-411)

<400> SEQUENCE: 49

His Asp Gly Tyr Thr Val Ser Trp Asn Thr Val Glu Asp Ser Ile Ile
1               5                   10                  15

Arg Thr Gly Phe Gln
            20

<210> SEQ ID NO 50
<211> LENGTH: 21
<212> TYPE: PRT
<213> ORGANISM: artificial sequence
<220> FEATURE:
<223> OTHER INFORMATION: synthetic peptide (N399K variant 391-411)

<400> SEQUENCE: 50

His Asp Gly Tyr Thr Val Ser Trp Lys Thr Val Glu Asp Ser Ile Ile
1               5                   10                  15

Arg Thr Gly Phe Gln
            20
```

<210> SEQ ID NO 51
<211> LENGTH: 21
<212> TYPE: PRT
<213> ORGANISM: artificial sequence
<220> FEATURE:
<223> OTHER INFORMATION: synthetic peptide (V401Q variant 391-411)

<400> SEQUENCE: 51

His Asp Gly Tyr Thr Val Ser Trp Asn Thr Gln Glu Asp Ser Ile Ile
1               5                   10                  15

Arg Thr Gly Phe Gln
            20

<210> SEQ ID NO 52
<211> LENGTH: 21
<212> TYPE: PRT
<213> ORGANISM: artificial sequence
<220> FEATURE:
<223> OTHER INFORMATION: synthetic peptide (N399K/V401Q variant 391-411)

<400> SEQUENCE: 52

His Asp Gly Tyr Thr Val Ser Trp Lys Thr Gln Glu Asp Ser Ile Ile
1               5                   10                  15

Arg Thr Gly Phe Gln
            20

<210> SEQ ID NO 53
<211> LENGTH: 9
<212> TYPE: PRT
<213> ORGANISM: artificial sequence
<220> FEATURE:
<223> OTHER INFORMATION: synthetic peptide (DTR1 396-404)

<400> SEQUENCE: 53

Val Ser Trp Asn Thr Val Glu Asp Ser
1               5

<210> SEQ ID NO 54
<211> LENGTH: 9
<212> TYPE: PRT
<213> ORGANISM: artificial sequence
<220> FEATURE:
<223> OTHER INFORMATION: synthetic peptide (DTR1 394-402)

<400> SEQUENCE: 54

Tyr Thr Val Ser Trp Asn Thr Val Glu
1               5

<210> SEQ ID NO 55
<211> LENGTH: 9
<212> TYPE: PRT
<213> ORGANISM: artificial sequence
<220> FEATURE:
<223> OTHER INFORMATION: synthetic peptide (DTR1 398-406)

<400> SEQUENCE: 55

Trp Asn Thr Val Glu Asp Ser Ile Ile
1               5

<210> SEQ ID NO 56
<211> LENGTH: 9
<212> TYPE: PRT
<213> ORGANISM: artificial sequence
<220> FEATURE:
<223> OTHER INFORMATION: synthetic peptide (N399K variant 398-406)

```
<400> SEQUENCE: 56

Trp Lys Thr Val Glu Asp Ser Ile Ile
1               5

<210> SEQ ID NO 57
<211> LENGTH: 9
<212> TYPE: PRT
<213> ORGANISM: artificial sequence
<220> FEATURE:
<223> OTHER INFORMATION: synthetic peptide (N399K variant 396-404)

<400> SEQUENCE: 57

Val Ser Trp Lys Thr Val Glu Asp Ser
1               5

<210> SEQ ID NO 58
<211> LENGTH: 9
<212> TYPE: PRT
<213> ORGANISM: artificial sequence
<220> FEATURE:
<223> OTHER INFORMATION: synthetic peptide (V401Q variant 394-402)

<400> SEQUENCE: 58

Tyr Thr Val Ser Trp Asn Thr Gln Glu
1               5

<210> SEQ ID NO 59
<211> LENGTH: 15
<212> TYPE: PRT
<213> ORGANISM: artificial sequence
<220> FEATURE:
<223> OTHER INFORMATION: synthetic peptide (DTR1 427-441)

<400> SEQUENCE: 59

Leu Pro Ile Ala Gly Val Leu Leu Pro Thr Ile Pro Gly Lys Leu
1               5                   10                  15

<210> SEQ ID NO 60
<211> LENGTH: 15
<212> TYPE: PRT
<213> ORGANISM: artificial sequence
<220> FEATURE:
<223> OTHER INFORMATION: synthetic peptide (L427Q variant 427-441)

<400> SEQUENCE: 60

Gln Pro Ile Ala Gly Val Leu Leu Pro Thr Ile Pro Gly Lys Leu
1               5                   10                  15

<210> SEQ ID NO 61
<211> LENGTH: 15
<212> TYPE: PRT
<213> ORGANISM: artificial sequence
<220> FEATURE:
<223> OTHER INFORMATION: synthetic peptide (T436K variant 427-441)

<400> SEQUENCE: 61

Leu Pro Ile Ala Gly Val Leu Leu Pro Lys Ile Pro Gly Lys Leu
1               5                   10                  15

<210> SEQ ID NO 62
<211> LENGTH: 15
<212> TYPE: PRT
<213> ORGANISM: artificial sequence
<220> FEATURE:
<223> OTHER INFORMATION: synthetic peptide (L427Q/T436K variant 427-441)
```

<400> SEQUENCE: 62

Gln Pro Ile Ala Gly Val Leu Leu Pro Lys Ile Pro Gly Lys Leu
1               5                   10                  15

<210> SEQ ID NO 63
<211> LENGTH: 9
<212> TYPE: PRT
<213> ORGANISM: artificial sequence
<220> FEATURE:
<223> OTHER INFORMATION: synthetic peptide (DTR1 432-440)

<400> SEQUENCE: 63

Val Leu Leu Pro Thr Ile Pro Gly Lys
1               5

<210> SEQ ID NO 64
<211> LENGTH: 9
<212> TYPE: PRT
<213> ORGANISM: artificial sequence
<220> FEATURE:
<223> OTHER INFORMATION: synthetic peptide (T436K variant 432-440)

<400> SEQUENCE: 64

Val Leu Leu Pro Lys Ile Pro Gly Lys
1               5

<210> SEQ ID NO 65
<211> LENGTH: 9
<212> TYPE: PRT
<213> ORGANISM: artificial sequence
<220> FEATURE:
<223> OTHER INFORMATION: synthetic peptide (DTR1 433-441)

<400> SEQUENCE: 65

Leu Leu Pro Thr Ile Pro Gly Lys Leu
1               5

<210> SEQ ID NO 66
<211> LENGTH: 9
<212> TYPE: PRT
<213> ORGANISM: artificial sequence
<220> FEATURE:
<223> OTHER INFORMATION: synthetic peptide (DTR1 427-435)

<400> SEQUENCE: 66

Leu Pro Ile Ala Gly Val Leu Leu Pro
1               5

<210> SEQ ID NO 67
<211> LENGTH: 15
<212> TYPE: PRT
<213> ORGANISM: artificial sequence
<220> FEATURE:
<223> OTHER INFORMATION: synthetic peptide (DTR1 451-465)

<400> SEQUENCE: 67

Ser Val Asn Gly Arg Lys Ile Arg Met Arg Cys Arg Ala Ile Asp
1               5                   10                  15

<210> SEQ ID NO 68
<211> LENGTH: 15
<212> TYPE: PRT
<213> ORGANISM: artificial sequence
<220> FEATURE:
<223> OTHER INFORMATION: synthetic peptide (I457D variant 451-465)

<400> SEQUENCE: 68

```
Ser Val Asn Gly Arg Lys Asp Arg Met Arg Cys Arg Ala Ile Asp
1               5                   10                  15

<210> SEQ ID NO 69
<211> LENGTH: 15
<212> TYPE: PRT
<213> ORGANISM: artificial sequence
<220> FEATURE:
<223> OTHER INFORMATION: synthetic peptide (I457E variant 451-465)

<400> SEQUENCE: 69

Ser Val Asn Gly Arg Lys Glu Arg Met Arg Cys Arg Ala Ile Asp
1               5                   10                  15

<210> SEQ ID NO 70
<211> LENGTH: 15
<212> TYPE: PRT
<213> ORGANISM: artificial sequence
<220> FEATURE:
<223> OTHER INFORMATION: synthetic peptide (V452T variant 451-465)

<400> SEQUENCE: 70

Ser Thr Asn Gly Arg Lys Ile Arg Met Arg Cys Arg Ala Ile Asp
1               5                   10                  15

<210> SEQ ID NO 71
<211> LENGTH: 15
<212> TYPE: PRT
<213> ORGANISM: artificial sequence
<220> FEATURE:
<223> OTHER INFORMATION: synthetic peptide (R460T variant 451-465)

<400> SEQUENCE: 71

Ser Val Asn Gly Arg Lys Ile Arg Met Thr Cys Arg Ala Ile Asp
1               5                   10                  15

<210> SEQ ID NO 72
<211> LENGTH: 15
<212> TYPE: PRT
<213> ORGANISM: artificial sequence
<220> FEATURE:
<223> OTHER INFORMATION: synthetic peptide (A463D variant 451-465)

<400> SEQUENCE: 72

Ser Val Asn Gly Arg Lys Ile Arg Met Arg Cys Arg Asp Ile Asp
1               5                   10                  15

<210> SEQ ID NO 73
<211> LENGTH: 15
<212> TYPE: PRT
<213> ORGANISM: artificial sequence
<220> FEATURE:
<223> OTHER INFORMATION: synthetic peptide (V452T/R460T/A463D variant
      451-465)

<400> SEQUENCE: 73

Ser Thr Asn Gly Arg Lys Ile Arg Met Thr Cys Arg Asp Ile Asp
1               5                   10                  15

<210> SEQ ID NO 74
<211> LENGTH: 9
<212> TYPE: PRT
<213> ORGANISM: artificial sequence
<220> FEATURE:
<223> OTHER INFORMATION: synthetic peptide (DTR1 457-465)

<400> SEQUENCE: 74
```

```
Ile Arg Met Arg Cys Arg Ala Ile Asp
1               5
```

<210> SEQ ID NO 75
<211> LENGTH: 9
<212> TYPE: PRT
<213> ORGANISM: artificial sequence
<220> FEATURE:
<223> OTHER INFORMATION: synthetic peptide (R460T variant 457-465)

<400> SEQUENCE: 75

```
Ile Arg Met Thr Cys Arg Ala Ile Asp
1               5
```

<210> SEQ ID NO 76
<211> LENGTH: 9
<212> TYPE: PRT
<213> ORGANISM: artificial sequence
<220> FEATURE:
<223> OTHER INFORMATION: synthetic peptide (A463D variant 457-465)

<400> SEQUENCE: 76

```
Ile Arg Met Arg Cys Arg Asp Ile Asp
1               5
```

<210> SEQ ID NO 77
<211> LENGTH: 9
<212> TYPE: PRT
<213> ORGANISM: artificial sequence
<220> FEATURE:
<223> OTHER INFORMATION: synthetic peptide (V452T/R460T/A463D variant
      451-465)

<400> SEQUENCE: 77

```
Ile Arg Met Thr Cys Arg Asp Ile Asp
1               5
```

<210> SEQ ID NO 78
<211> LENGTH: 9
<212> TYPE: PRT
<213> ORGANISM: artificial sequence
<220> FEATURE:
<223> OTHER INFORMATION: synthetic peptide (DTR1 452-460)

<400> SEQUENCE: 78

```
Val Asn Gly Arg Lys Ile Arg Met Arg
1               5
```

<210> SEQ ID NO 79
<211> LENGTH: 9
<212> TYPE: PRT
<213> ORGANISM: artificial sequence
<220> FEATURE:
<223> OTHER INFORMATION: synthetic peptide (R460T variant 452-460)

<400> SEQUENCE: 79

```
Val Asn Gly Arg Lys Ile Arg Met Thr
1               5
```

<210> SEQ ID NO 80
<211> LENGTH: 28
<212> TYPE: PRT
<213> ORGANISM: artificial sequence
<220> FEATURE:
<223> OTHER INFORMATION: synthetic peptide (DTR1 475-502)

<400> SEQUENCE: 80

Ser Pro Val Tyr Val Gly Asn Gly Val His Ala Asn Leu His Val Ala
1               5                   10                  15

Phe His Arg Ser Ser Ser Glu Lys Ile His Ser Asn
            20                  25

<210> SEQ ID NO 81
<211> LENGTH: 28
<212> TYPE: PRT
<213> ORGANISM: artificial sequence
<220> FEATURE:
<223> OTHER INFORMATION: synthetic peptide (Y478T variant 475-502)

<400> SEQUENCE: 81

Ser Pro Val Thr Val Gly Asn Gly Val His Ala Asn Leu His Val Ala
1               5                   10                  15

Phe His Arg Ser Ser Ser Glu Lys Ile His Ser Asn
            20                  25

<210> SEQ ID NO 82
<211> LENGTH: 28
<212> TYPE: PRT
<213> ORGANISM: artificial sequence
<220> FEATURE:
<223> OTHER INFORMATION: synthetic peptide (V483D variant 475-502)

<400> SEQUENCE: 82

Ser Pro Val Tyr Val Gly Asn Gly Asp His Ala Asn Leu His Val Ala
1               5                   10                  15

Phe His Arg Ser Ser Ser Glu Lys Ile His Ser Asn
            20                  25

<210> SEQ ID NO 83
<211> LENGTH: 28
<212> TYPE: PRT
<213> ORGANISM: artificial sequence
<220> FEATURE:
<223> OTHER INFORMATION: synthetic peptide (V483E variant 475-502)

<400> SEQUENCE: 83

Ser Pro Val Tyr Val Gly Asn Gly Glu His Ala Asn Leu His Val Ala
1               5                   10                  15

Phe His Arg Ser Ser Ser Glu Lys Ile His Ser Asn
            20                  25

<210> SEQ ID NO 84
<211> LENGTH: 28
<212> TYPE: PRT
<213> ORGANISM: artificial sequence
<220> FEATURE:
<223> OTHER INFORMATION: synthetic peptide (V483H variant 475-502)

<400> SEQUENCE: 84

Ser Pro Val Tyr Val Gly Asn Gly His His Ala Asn Leu His Val Ala
1               5                   10                  15

Phe His Arg Ser Ser Ser Glu Lys Ile His Ser Asn
            20                  25

<210> SEQ ID NO 85
<211> LENGTH: 28
<212> TYPE: PRT
<213> ORGANISM: artificial sequence
<220> FEATURE:
<223> OTHER INFORMATION: synthetic peptide (V483Q variant 475-502)

```
<400> SEQUENCE: 85

Ser Pro Val Tyr Val Gly Asn Gly Gln His Ala Asn Leu His Val Ala
1               5                   10                  15

Phe His Arg Ser Ser Ser Glu Lys Ile His Ser Asn
            20                  25

<210> SEQ ID NO 86
<211> LENGTH: 28
<212> TYPE: PRT
<213> ORGANISM: artificial sequence
<220> FEATURE:
<223> OTHER INFORMATION: synthetic peptide (A490G variant 475-502)

<400> SEQUENCE: 86

Ser Pro Val Tyr Val Gly Asn Gly Val His Ala Asn Leu His Val Gly
1               5                   10                  15

Phe His Arg Ser Ser Ser Glu Lys Ile His Ser Asn
            20                  25

<210> SEQ ID NO 87
<211> LENGTH: 28
<212> TYPE: PRT
<213> ORGANISM: artificial sequence
<220> FEATURE:
<223> OTHER INFORMATION: synthetic peptide (H492E variant 475-502)

<400> SEQUENCE: 87

Ser Pro Val Tyr Val Gly Asn Gly Val His Ala Asn Leu His Val Ala
1               5                   10                  15

Phe Glu Arg Ser Ser Ser Glu Lys Ile His Ser Asn
            20                  25

<210> SEQ ID NO 88
<211> LENGTH: 28
<212> TYPE: PRT
<213> ORGANISM: artificial sequence
<220> FEATURE:
<223> OTHER INFORMATION: synthetic peptide (S494K variant 475-502)

<400> SEQUENCE: 88

Ser Pro Val Tyr Val Gly Asn Gly Val His Ala Asn Leu His Val Ala
1               5                   10                  15

Phe His Arg Lys Ser Ser Glu Lys Ile His Ser Asn
            20                  25

<210> SEQ ID NO 89
<211> LENGTH: 28
<212> TYPE: PRT
<213> ORGANISM: artificial sequence
<220> FEATURE:
<223> OTHER INFORMATION: synthetic peptide (S496K variant 475-502)

<400> SEQUENCE: 89

Ser Pro Val Tyr Val Gly Asn Gly Val His Ala Asn Leu His Val Ala
1               5                   10                  15

Phe His Arg Ser Ser Lys Glu Lys Ile His Ser Asn
            20                  25

<210> SEQ ID NO 90
<211> LENGTH: 28
<212> TYPE: PRT
<213> ORGANISM: artificial sequence
<220> FEATURE:
<223> OTHER INFORMATION: synthetic peptide
```

(Y478T/A490G/H492E/S494K/S496K variant 475-502)

<400> SEQUENCE: 90

Ser Pro Val Thr Val Gly Asn Gly Val His Ala Asn Leu His Val Gly
1               5                   10                  15

Phe Glu Arg Lys Ser Lys Glu Lys Ile His Ser Asn
            20                  25

<210> SEQ ID NO 91
<211> LENGTH: 9
<212> TYPE: PRT
<213> ORGANISM: artificial sequence
<220> FEATURE:
<223> OTHER INFORMATION: synthetic peptide (DTR1 478-486)

<400> SEQUENCE: 91

Tyr Val Gly Asn Gly Val His Ala Asn
1               5

<210> SEQ ID NO 92
<211> LENGTH: 9
<212> TYPE: PRT
<213> ORGANISM: artificial sequence
<220> FEATURE:
<223> OTHER INFORMATION: synthetic peptide (DTR1 491-499)

<400> SEQUENCE: 92

Phe His Arg Ser Ser Ser Glu Lys Ile
1               5

<210> SEQ ID NO 93
<211> LENGTH: 9
<212> TYPE: PRT
<213> ORGANISM: artificial sequence
<220> FEATURE:
<223> OTHER INFORMATION: synthetic peptide (DTR1 477-485)

<400> SEQUENCE: 93

Val Tyr Val Gly Asn Gly Val His Ala
1               5

<210> SEQ ID NO 94
<211> LENGTH: 9
<212> TYPE: PRT
<213> ORGANISM: artificial sequence
<220> FEATURE:
<223> OTHER INFORMATION: synthetic peptide (DTR1 487-495)

<400> SEQUENCE: 94

Leu His Val Ala Phe His Arg Ser Ser
1               5

<210> SEQ ID NO 95
<211> LENGTH: 9
<212> TYPE: PRT
<213> ORGANISM: artificial sequence
<220> FEATURE:
<223> OTHER INFORMATION: synthetic peptide (V483D variant 478-486)

<400> SEQUENCE: 95

Tyr Val Gly Asn Gly Asp His Ala Asn
1               5

<210> SEQ ID NO 96
<211> LENGTH: 9
<212> TYPE: PRT

```
<213> ORGANISM: artificial sequence
<220> FEATURE:
<223> OTHER INFORMATION: synthetic peptide (V483H variant 477-485)

<400> SEQUENCE: 96

Val Tyr Val Gly Asn Gly His His Ala
1               5

<210> SEQ ID NO 97
<211> LENGTH: 9
<212> TYPE: PRT
<213> ORGANISM: artificial sequence
<220> FEATURE:
<223> OTHER INFORMATION: synthetic peptide (V483Q variant 477-485)

<400> SEQUENCE: 97

Val Tyr Val Gly Asn Gly Gln His Ala
1               5

<210> SEQ ID NO 98
<211> LENGTH: 9
<212> TYPE: PRT
<213> ORGANISM: artificial sequence
<220> FEATURE:
<223> OTHER INFORMATION: synthetic peptide (V483Q variant 478-486)

<400> SEQUENCE: 98

Tyr Val Gly Asn Gly Gln His Ala Asn
1               5

<210> SEQ ID NO 99
<211> LENGTH: 9
<212> TYPE: PRT
<213> ORGANISM: artificial sequence
<220> FEATURE:
<223> OTHER INFORMATION: synthetic peptide (A490G variant 487-495)

<400> SEQUENCE: 99

Leu His Val Gly Phe His Arg Ser Ser
1               5

<210> SEQ ID NO 100
<211> LENGTH: 8
<212> TYPE: PRT
<213> ORGANISM: artificial sequence
<220> FEATURE:
<223> OTHER INFORMATION: synthetic peptide (H492E variant 491-499)

<400> SEQUENCE: 100

Phe Glu Arg Ser Ser Ser Glu Lys
1               5

<210> SEQ ID NO 101
<211> LENGTH: 9
<212> TYPE: PRT
<213> ORGANISM: artificial sequence
<220> FEATURE:
<223> OTHER INFORMATION: synthetic peptide (H492E variant 487-495)

<400> SEQUENCE: 101

Leu His Val Ala Phe Glu Arg Ser Ser
1               5

<210> SEQ ID NO 102
<211> LENGTH: 9
<212> TYPE: PRT
<213> ORGANISM: artificial sequence
```

```
<220> FEATURE:
<223> OTHER INFORMATION: synthetic peptide (S494K variant 491-499)

<400> SEQUENCE: 102

Phe His Arg Lys Ser Ser Glu Lys Ile
1               5

<210> SEQ ID NO 103
<211> LENGTH: 9
<212> TYPE: PRT
<213> ORGANISM: artificial sequence
<220> FEATURE:
<223> OTHER INFORMATION: synthetic peptide (S494K variant 487-495)

<400> SEQUENCE: 103

Leu His Val Ala Phe His Arg Lys Ser
1               5

<210> SEQ ID NO 104
<211> LENGTH: 9
<212> TYPE: PRT
<213> ORGANISM: artificial sequence
<220> FEATURE:
<223> OTHER INFORMATION: synthetic peptide (S494K variant 489-497)

<400> SEQUENCE: 104

Val Ala Phe His Arg Lys Ser Ser Glu
1               5

<210> SEQ ID NO 105
<211> LENGTH: 9
<212> TYPE: PRT
<213> ORGANISM: artificial sequence
<220> FEATURE:
<223> OTHER INFORMATION: synthetic peptide (S496K variant 491-499)

<400> SEQUENCE: 105

Phe His Arg Ser Ser Lys Glu Lys Ile
1               5

<210> SEQ ID NO 106
<211> LENGTH: 15
<212> TYPE: PRT
<213> ORGANISM: artificial sequence
<220> FEATURE:
<223> OTHER INFORMATION: synthetic peptide (DTR1 506-520)

<400> SEQUENCE: 106

Ser Asp Ser Ile Gly Val Leu Gly Tyr Gln Lys Thr Val Asp His
1               5                   10                  15

<210> SEQ ID NO 107
<211> LENGTH: 15
<212> TYPE: PRT
<213> ORGANISM: artificial sequence
<220> FEATURE:
<223> OTHER INFORMATION: synthetic peptide (T517D variant 506-520)

<400> SEQUENCE: 107

Ser Asp Ser Ile Gly Val Leu Gly Tyr Gln Lys Asp Val Asp His
1               5                   10                  15

<210> SEQ ID NO 108
<211> LENGTH: 15
<212> TYPE: PRT
<213> ORGANISM: artificial sequence
<220> FEATURE:
```

-continued

```
<223> OTHER INFORMATION: synthetic peptide (T517E variant 506-520)

<400> SEQUENCE: 108

Ser Asp Ser Ile Gly Val Leu Gly Tyr Gln Lys Glu Val Asp His
1               5                   10                  15

<210> SEQ ID NO 109
<211> LENGTH: 9
<212> TYPE: PRT
<213> ORGANISM: artificial sequence
<220> FEATURE:
<223> OTHER INFORMATION: synthetic peptide (DTR1 512-520)

<400> SEQUENCE: 109

Leu Gly Tyr Gln Lys Thr Val Asp His
1               5

<210> SEQ ID NO 110
<211> LENGTH: 9
<212> TYPE: PRT
<213> ORGANISM: artificial sequence
<220> FEATURE:
<223> OTHER INFORMATION: synthetic peptide (A490G variant 479-497)

<400> SEQUENCE: 110

Val Gly Phe His Arg Ser Ser Ser Glu
1               5
```